United States Patent
Budman et al.

(10) Patent No.: US 11,964,041 B2
(45) Date of Patent: Apr. 23, 2024

(54) COMPOSITIONS COMPRISING LEVAN AND USE THEREOF

(71) Applicant: GAN SHMUEL FOODS LTD., Gan Shmuel (IL)

(72) Inventors: Eli Budman, Zichron Yaacov (IL); Yuval Katzir, Kibbutz Gan Shmuel (IL)

(73) Assignee: GAN SHMUEL FOODS LTD., Gan Shmuel (IL)

( * ) Notice: Subject to any disclaimer, the term of this patent is extended or adjusted under 35 U.S.C. 154(b) by 0 days.

(21) Appl. No.: 17/047,523

(22) PCT Filed: Apr. 15, 2019

(86) PCT No.: PCT/IL2019/050426
§ 371 (c)(1),
(2) Date: Oct. 14, 2020

(87) PCT Pub. No.: WO2019/202591
PCT Pub. Date: Oct. 24, 2019

(65) Prior Publication Data
US 2021/0154124 A1 May 27, 2021

Related U.S. Application Data

(60) Provisional application No. 62/657,850, filed on Apr. 15, 2018, provisional application No. 62/736,552, filed on Sep. 26, 2018.

(51) Int. Cl.
| | | |
|---|---|---|
| *A61K 8/73* | (2006.01) | |
| *A61K 8/60* | (2006.01) | |
| *A61K 8/891* | (2006.01) | |
| *A61K 31/733* | (2006.01) | |
| *A61Q 19/08* | (2006.01) | |
| *C08L 5/00* | (2006.01) | |

(52) U.S. Cl.
CPC .......... *A61K 8/73* (2013.01); *A61K 8/60* (2013.01); *A61K 8/891* (2013.01); *A61K 31/733* (2013.01); *A61Q 19/08* (2013.01); *C08L 5/00* (2013.01)

(58) Field of Classification Search
CPC ........ A61K 8/73; A61K 8/891; A61K 31/733; A61K 8/60; A61Q 19/08; C08L 5/00
USPC ........................................... 514/54
See application file for complete search history.

(56) References Cited

FOREIGN PATENT DOCUMENTS

| | | | | |
|---|---|---|---|---|
| FR | 2999425 | A1 | 6/2014 | |
| KR | 20130087262 | A | 8/2013 | |
| WO | WO-2005051102 | A1 * | 6/2005 | ............. A23L 33/10 |
| WO | 2010061383 | A1 | 6/2010 | |
| WO | 2015075440 | A1 | 5/2015 | |

OTHER PUBLICATIONS

Gan Shmuel Foods ltd; "1.1-GS Levan—LMW 28-30% (Solution) Product Specification Gan Shmuel—31.10", Date: Oct. 31, 2017.*
Soon Ah Kang, Ki-Hyo Jang, Jeong-Woo Seo, Ki Ho Kim, Young Heui Kim, Dina Rairakhwada, Mi Young Seo, Jae Ok Lee, Sang Do Ha, Chul-Ho Kim and Sang-Ki Rhee Levan: Applications and Perspectives from: Microbial Production of Biopolymers and Polymer Precursors: Applications and Perspectives (Edited by: Bernd H. A. Rehm). Caister Academic Press, U.K. (2009).
Nakapong S, Pichyangkura R, Ito K, Iizuka M, Pongsawasdi P. High expression level of levansucrase from Bacillus licheniformis RN-01 and synthesis of levan nanoparticles. Int J Biol Macromol. Mar. 2013;54:30-6. doi: 10.1016/j.jbiomac.2012.11.017. Epub Nov. 28, 2012. PMID: 23219733.
Tian, F., Khodadadi, M., & Karboune, S. (2014). Optimization of levansucrase/endo-inulinase bi-enzymatic system for the production of fructooligosaccharides and oligolevans from sucrose. Journal of Molecular Catalysis B: Enzymatic, 109, 85-93.
Goldman D, Lavid N, Schwartz A, Shoham G, Danino D, Shoham Y. Two active forms of Zymomonas mobilis levansucrase. An ordered microfibril structure of the enzyme promotes levan polymerization. J Biol Chem. Nov. 21, 2008;283(47):32209-17. doi: 10.1074/jbc.M805985200. Epub Sep. 22, 2008. PMID: 18809687.

* cited by examiner

*Primary Examiner* — Layla D Berry
(74) *Attorney, Agent, or Firm* — The Roy Gross Law Firm, LLC; Roy Gross

(57) ABSTRACT

A composition comprised of a plurality of levan oligomers, wherein at least 70% (w/w) of said plurality of levan oligomers are characterized by: (i) weight average molecular weights ($M_w$) of 540 to 1000 g/mole, and (ii) a dispersity index () of less than 2 is disclosed herein. Uses of the levan composition, such as, as a feed additive, growth promoter and for improving the rejuvenation and healing of a human skin, are also disclosed.

19 Claims, 33 Drawing Sheets

COMPOSITIONS COMPRISING LEVAN AND USE THEREOF

CROSS REFERENCE TO RELATED APPLICATIONS

This application is a National Phase of PCT Patent Application No. PCT/IL2019/050426 having International filing date of Apr. 15, 2019, which claims the benefit of priority under 35 U.S.C. § 119(e) of U.S. Provisional Patent Application No. 62/657,850 filed Apr. 15, 2018 and U.S. Provisional Patent Application No. 62/736,552 filed Sep. 26, 2018, both entitled "COMPOSITIONS COMPRISING LEVAN AND USE THEREOF". The contents of the above applications which are all incorporated by reference as if fully set forth herein in their entirety.

FIELD OF THE INVENTION

The present invention, in some embodiments thereof, relates to a levan composition, and to the use thereof e.g., for cosmetic products.

BACKGROUND OF THE INVENTION

Human skin, as a primary protective barrier, protects the vital organs of the body from external insult such as changes in temperature and humidity, ultraviolet (UV) rays and contaminants, and plays an important role in the regulation of biological homeostasis such as thermoregulation.

Skin aging is driven by intrinsic (chronological aging) and extrinsic (environmental) factors, including UV radiation exposure (i.e., "photoaging"), environmental toxins, pollutants, and smoking. This results in a reduction in the functioning capacity of the barrier so that harmful stimuli penetrate the stratum corneum more easily, leading to damage, for example, of the underlying dermal layers, degradation of collagen and elastin, and eventually manifests in appearance as wrinkling and skin atrophy.

Moreover, as skin ages, it shows skin aging signs such as loss of elasticity, keratinization, formation of skin wrinkles and skin contraction. The cause of this skin aging can be classified as internal factors such as cell gene transformation and cell tissue change, and external factors such as ultraviolet and humidity.

SUMMARY OF THE INVENTION

The present invention, in some embodiments thereof, relates to a levan composition, and to the use thereof e.g., for cosmetic products.

According to an aspect of the present invention, there is provided a composition comprising a plurality of levan oligomers, wherein at least 70% (w/w) of the plurality of levan oligomers are characterized by: (i) weight average molecular weights ($M_W$) of 540 to 1000 g/mol, and (ii) a dispersity index (Đ) of less than 2.

In some embodiments, the composition further comprises up to 30% levan polymers, by total moles, or in some embodiments, by total weight of the oligomers and the polymers, wherein the polymers are characterized by $M_W$ of above 10,000 g/mol.

In some embodiments, the $M_W$ of the polymers is above 30,000 g/mol.

In some embodiments, the oligomers are characterized by less than 1% branching.

In some embodiments, the polymers are characterized by less than 10% branching.

In some embodiments, at least 60% of the levan polymers are in the form of an aggregate having an apparent relative density of 20 to 50.

In some embodiments, the composition is a cosmetic or cosmeceutical composition.

In some embodiments, the composition is formulated for topical administration.

In some embodiments, the composition is formulated in the form selected from the group consisting of: aqueous solution, cream, lotion, water in oil or oil in water emulsion, multiple emulsion, silicone emulsion, microemulsion, foam, gel and an aqueous solution with a co-solvent.

In some embodiments, the composition further comprises one or more components selected from the group consisting of: monosaccharides, disaccharides, buffer, a preservative, one or more additives, or any combination thereof.

In some embodiments, the levan oligomers and polymers are present at a concentration of at least 0.1%, by weight relative to a total weight of the total composition.

In some embodiments, a total concentration of the levan oligomers and the levan polymers is at least 0.1%, by weight relative to a total weight of the total composition. In some embodiments, a total concentration of the levan oligomers and the levan polymers is at least 0.3%, by weight relative to a total weight of the total composition.

In some embodiments, a total concentration of the levan oligomers and the levan polymers is at least 30%, by weight relative to a total weight of the total composition.

In some embodiments, a weight ratio of a total amount of the levan oligomers and the levan polymers to the mono- and/or di-saccharides is at least 1.

In some embodiments, the monosaccharides are selected from the group consisting of: glucose, fructose, and a combination thereof.

In some embodiments, the disaccharides comprise sucrose.

In some embodiments, the one or more additives are present at a concentration of less than 5% by weight relative to a total weight of the composition.

In some embodiments, the composition is for use as a food additive, dietary supplement, feed additive, or prebiotics. In some embodiments, the composition improves the feed conversion ratio (i.e. the weight of ingested feed relative to weight gain) of an animal. In some embodiments, the composition is a growth promoter.

In some embodiments, the composition is for use in preventing or treating a skin condition selected from the group consisting of: fine lines, wrinkles, discoloration, uneven pigmentation, sagging, enlarged pores, blemishes, and a combination thereof.

According to another aspect, there is provided a method for improving the rejuvenation and healing of a skin, the method comprising the step of applying the composition in an embodiment thereof on a region of the skin.

According to another aspect, there is provided a method for improving feed conversion ratio, the method comprising the step of providing feed comprising the composition of the invention to an animal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawing in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A, and 1B, respectively) of the disclosed levan oligomers. The peak differences of 162 grams per molecule is assigned to a fructose molecule;

DETAILED DESCRIPTION

Figure 1A:
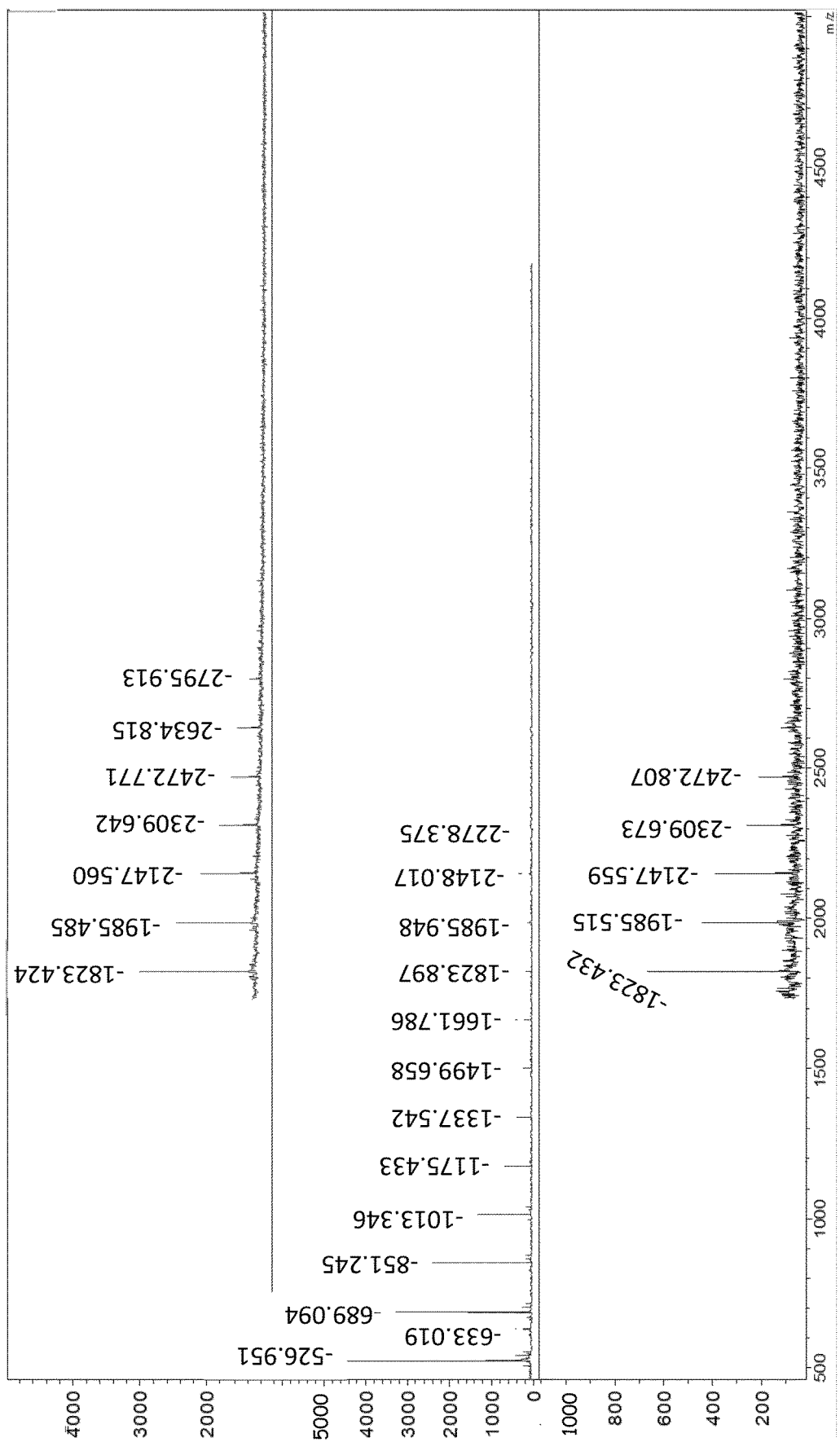
FIGS. 1A-1B present exemplary Matrix Assisted Laser Ionization Time-Of-Flight (MALDI-TOF) mass spectra of samples (denoted as "2845", and "2847"

The present invention, in some embodiments thereof, relates to levan composition, and to the use thereof, including but not limited to in cosmetic products, e.g., for protecting the human skin, scalp or mucous membrane, and for the production of cosmetic preparations for skin protection.

According to an aspect of some embodiments of the present invention, there is provided a composition comprising a plurality of levan oligomers, wherein at least 70% of the plurality of the levan oligomers are characterized by weight average molecular weights ($M_W$) of less than 5000 g/mol, less than 4000 g/mol, less than 3000 g/mol, less than 2000 g/mol, less than 1000 g/mol, or less than 800 g/mol.

In some embodiments, at least 70% of the plurality of the levan oligomers are characterized by weight average in the range of 5000 g/mol to 50 g/mol, 5000 g/mol to 100 g/mol, 5000 g/mol to 200 g/mol, 5000 g/mol to 400 g/mol, 5000 g/mol to 500 g/mol, 5000 g/mol to 750 g/mol, 4000 g/mol to 1000 g/mol, 3500 g/mol to 800 g/mol, 1000 g/mol to 800 g/mol, 1000 g/mol to 600 g/mol, or 900 g/mol to 600 g/mol, including any range therebetween.

In some embodiments, the composition comprises levan polymers.

As used hereinthroughout, the term "polymer" describes an organic substance composed of a plurality of e.g., more than 10 repeating structural units (backbone units), or more than 15 repeating structural units covalently connected to one another.

In some embodiments, the term "oligomer", as used herein, refers to a chemical compound with a finite number of structural units connected by covalent bonds. An oligomer has less monomeric units than the corresponding polymer. In some embodiments, the levan oligomer typically has between 3 to 15 monomeric units making up its structure. In some embodiments, the levan oligomer has 3 to 10 monomeric units. In some embodiments, the levan oligomer has 4 to 10 monomeric units. In some embodiments, the levan oligomer has 3 or 4 units.

In some embodiments, at least 70%, at least 80%, or at least 90% of the plurality of the levan oligomers are characterized by weight average molecular weights ($M_W$) of 540 g/mol to 800 g/mol, 540 g/mol to 700 g/mol, 540 g/mol to 800 g/mol, or 540 to 1000 g/mol, including any value and range therebetween.

In some embodiments, at least 50 to 80%, or at least 60 to 90%, of the plurality of the levan polymers are characterized by $M_W$ of 1000 Kg/mol to 10000 Kg/mol, 1000 Kg/mol to 7000 Kg/mol, 1000 Kg/mol to 50000 Kg/mol, 1000 Kg/mol to 3,000,000 Kg/mol, 1000 Kg/mol to 10,000,000 Kg/mol, including any value and range therebetween. In some embodiments, about 70% to 95%, about 80% to 95%, or about 90% to 95% of the plurality of the levan polymers are characterized by weight average molecular weights ($M_W$) of 1000 Kg/mol to 10000 Kg/mol, 1000 Kg/mol to 7000 Kg/mol, 1000 Kg/mol to 50000 Kg/mol, 1000 Kg/mol to 3,000,000 Kg/mol, 1000 Kg/mol to 10,000,000 Kg/mol, including any value and range therebetween.

In some embodiments, at least 80% of the plurality of the levan polymers are characterized by a dispersity index (Đ) of less than 8, less than 7.9, less than 7.8, less than 7.7, less than 7.6, less than 7.5, less than 7.4, less than 7.3, less than 7.2, less than 7.1, less than 7, less than 6.9, less than 6.8, less than 6.7, less than 6.6, less than 6.5, less than 6.4, less than 6.3, less than 6.2, less than 6.1, less than 6, less than 5.9, less than 5.8, less than 5.7, less than 5.6, less than 5.5, less than 5.4, less than 5.3, less than 5.2, less than 5.1, less than 5, less than 4.9, less than 4.8, less than 4.7, less than 4.6, less than 4.5, less than 4.4, less than 4.3, less than 4.2, less than 4.1, or less than 4.

In some embodiments, at least 70%, at least 80%, or at least 90%, of the plurality of the levan polymers are characterized by a dispersity index (Ð) of 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, or 8, including any value and range therebetween.

In some embodiments, at least 80% of the plurality of the levan oligomers are characterized by a dispersity index (Ð) of less than 3, less than 2.9, less than 2.8, less than 2.7, less than 2.6, less than 2.5, less than 2.4, less than 2.3, less than 2.2, less than 2.1, less than 2, less than 1.9, less than 1.8, less than 1.7, less than 1.6, less than 1.5, less than 1.4, less than 1.3, less than 1.2, or less than 1.1.

As used herein, "dispersity index", also termed in the art: "polydispersity index" (denoted hereinthroughout as: "Ð") refers to a measure of the distribution of molecular mass in a given polymer sample. The dispersity index is calculated by dividing the weight average molecular weight (Mw) by the number average molecular weight (Mn). As used herein, the term "weight average molecular weight" generally refers to a molecular weight measurement that depends on the contributions of polymer molecules according to their sizes. As used herein, the term "number average molecular weight" generally refers to a molecular weight measurement that is calculated by dividing the total weight of all the polymer molecules in a sample with the total number of polymer molecules in the sample. These terms are known by those of ordinary skill in the art.

Ð has a value always greater than 1, but as the polymer chains approach uniform chain length, the value of Ð approaches unity (1).

In some embodiments, the composition comprises at least 10%, at least 20%, at least 30%, at least 40%, at least 50%, at least 60%, at least 70%, or at least 80%, by weight, levan oligomers. In some embodiments, the composition further comprises 1%, 5%, 10%, 15%, 20%, 25%, 30%, 35%, 40%, 45%, or 50%, by weight, including any value and range therebetween, levan polymers.

In some embodiments, the term "levan" refers to a D-fructan which is characterized e.g., by β(2-6) binding of fructose molecules, reaching up to n (e.g., tens, hundreds, thousands and hundreds of thousand) fructose units per a carbohydrate chain. In some embodiments, the fructose molecules chain has a terminal glucose molecule. In some embodiments, the levan oligomers comprises 2-5, e.g., 2, 3, 4, or 5 fructose units. Further, "levan" as used herein should be understood to encompass levan derived from any source such as but not limited to: *Alectis indicus, Avicularia versicolor, Acetobacter suboxydans, Achromobacter* spp., *Actinomycenes* sp., *Actinomyces viscosus, Aerobacter aerogenes, Aerobacter levanicum, Aspergillus sydowi, Azotobacter chroococcum, Bacillus polymyxa, Bacillus licheniformis, Bacillus macerans, Bacillus megatherium, Bacillus mesentericus, Bacillus subtilis, Bacillus vulgatus, Corynbacterium laevaniformans, Erwinia herbicola, Gluconobacter oxydans, Leuconostoc mesenteroides, Odontomyces viscosus, Phytobacterium vitrosum, Phytomonas pruni, Psuedomonas Pluorescens, Pseudomonas Syringae, Pseudomonas prunicola, Rothis dentocariosa, Serratia kiliensis, Steptococcus bovis, Steptococcus mutans, Steptococcus salivarius, Xanthomonas campestris, Xanthomonas pruni,* or *Zymomonas mobilis*. In exemplary embodiments, the levan is obtained from *Zymomonas mobilis*. In some embodiments, the levan is obtained from *Pichia pastoris*.

In some embodiments, at least 70% of the disclosed oligomers has less than 5% branching. In some embodiments, at least 70% of the disclosed oligomers has less than 3% branching. In some embodiments, at least 70% of the disclosed oligomers has less than 1% branching.

In some embodiments, at least 80% of the disclosed oligomers has less than 5% branching. In some embodiments, at least 80% of the disclosed oligomers has less than 3% branching. In some embodiments, at least 80% of the disclosed oligomers has less than 1% branching.

As used herein, the term "branching", or any grammatical derivative thereof, is used to refer to an oligomer or polymer chain having branch points that connect three or more chain segments. Examples of branched oligomers or polymers include long chains having occasional and usually short branches including the same repeat units as the main chain (nominally termed a branched polymer).

In some embodiments, the plurality of the polymers is in the form of aggregate particles. In some embodiments, the size of the particles described herein represents an average or median size of a plurality of particles.

In some embodiments, a plurality of the particles has a uniform size.

By "uniform" or "homogenous" it is meant to refer to size distribution that varies within a range of less than e.g., ±60%, ±50%, ±40%, ±30%, ±20%, or ±10%, including any value therebetween.

In some embodiments, the particles are characterized by a median hydrodynamic radius.

In some embodiments, the particles are characterized by a median root-mean square radius.

The term "hydrodynamic radius" or "Stokes radius" is the effective radius of the molecules in a solution ($r_h$) as detected e.g., by dynamic light scattering (DLS).

In some embodiments, the particles are characterized by a median root-mean square radius ($r_{rms}$).

In some embodiments, the particles are characterized by a ratio of $r_{rms}/r_h$ (also referred to as: "structure factor") having a value of: 5:1 to 1:1, e.g., 5:1, 4:1, 3:1, 2:1, 1:1, including any value and range therebetween.

In some embodiments, at least e.g., 60%, of the disclosed levan polymeric aggregates are characterized by an apparent relative density of 20 to 50.

In some embodiments, at least e.g., 70% of the disclosed levan polymeric aggregates are characterized by an apparent relative density of 20 to 50.

In some embodiments, at least e.g., 80% of the disclosed levan polymeric aggregates are characterized by an apparent relative density of 20 to 50.

In some embodiments, the levan oligomers and/or polymers are present at a concentration of 10% to 80% by weight relative to a total weight of the composition.

In some embodiments, the levan oligomers and/or polymers are present at a concentration of 0.1% to 60% by weight relative to a total weight of the composition. In some embodiments, the levan oligomers and/or polymers are present at a concentration of 10% to 60% by weight relative to a total weight of the composition. In some embodiments, the levan oligomers and polymers are present are present at a concentration of 10%, 20%, 30%, 40%, 50%, or 50%, by weight relative to a total weight of the composition.

In some embodiments, the composition is in the form of a formulation.

In some embodiments, the composition is in the form of cosmetic or cosmeceutical composition.

In some embodiments, the composition further comprises about 1% to about 50% of sugars by weight relative to a total weight of the total composition, including any value and range therebetween. In some embodiments the composition further comprises about 10% of sugars. In some embodiments the composition further comprises about 20% of sugars. In some embodiments the composition further comprises 25% of sugars. In some embodiments the composition further comprises about 30% of sugars. In some embodiments the composition further comprises about 35% of sugars. In some embodiments the composition further comprises about 40% of sugars. In some embodiments the composition further comprises about 50% of sugars.

In some embodiments, the term "sugar" refers to monosaccharides or disaccharides including, without being limited thereto, glucose, fructose, galactose, sucrose, a disaccharide of glucose and fructose, or any combination thereof.

In some embodiments, a weight ratio of levan oligomers together with levan polymers to the mono- and di-saccharides is at least 0.5, or at least 1, or at least 1.5, or at least 2.

In some embodiments, the composition further comprises a buffer solution. In some embodiments, the composition further comprises 0.5% to 5%, by weight, buffer solution. In some embodiments, the composition further comprises 0.5% to 3%, by weight, buffer solution. In some embodiments, the composition further comprises 0.5%, 1%, 1.5%, 2%, 2.5%, or 3% by weight buffer solution, including any value and range therebetween.

In some embodiments, the buffer comprises one or more salts selected from, without being limited thereto, sodium citrate, and potassium hydroxide.

In some embodiments, the composition has a pH higher than 4. In some embodiments, the pH of the composition is about 5.5, about 6, or about 7, including any value therebetween. In some embodiments, the composition further comprises an acid, e.g., citric acid.

In some embodiments, the composition is formulated in the form selected from, without being limited thereto, aqueous solution, cream, lotion, water in oil or oil in water emulsion, multiple emulsion, silicone emulsion, microemulsion, gel, foam and an aqueous solution with a co-solvent. Each possibility represents a separate embodiment of the present invention.

In some embodiments, the composition is a cosmetic composition formulated for topical administration.

In some embodiments, the composition is formulated as a prebiotic composition. The term "prebiotics" refers to non-digestible food ingredients that may beneficially affect the host by selectively stimulating the growth and/or activity of one or a limited number of cells in the colon or can improve the health of the host.

The term "topical administration", as used herein, refers to administration through body surfaces, preferably through or on skin.

In some embodiments, the composition of the invention is formulated for application to the skin of a subject in need thereof.

In some embodiments, the composition of the invention is a skin rejuvenation composition for use in treatment of a skin condition.

The term "skin", as used herein, refers to any epidermal surface and can also include, without limitation, the surface of the face and neck, hands, elbows, upper arm region, knees, thighs, legs, feet, breasts, chest, stomach, buttocks, sex organs, vagina, or oral cavity.

In more specific embodiments, skin cells may include epidermal and dermal cells, comprising fibroblasts, keratinocytes, Langerhans cells, Merkel cells and melanocytes.

The term "rejuvenation" is intended to refer to the reversal or mitigation of the aging process, or any other processes (e.g. abrasion caused by a fall, burns, etc.) that may have damaged or caused an accumulation of damage to macromolecules, cells, tissues and organs, including the skin. In some embodiments, rejuvenation is the repair of any of such damage.

In some embodiments, the composition is for use in preventing or treating a skin condition skin selected from, without being limited thereto, fine lines, wrinkles, discoloration, uneven pigmentation, sagging, enlarged pores, rough skin, wrinkle, an age spot, a photo damage, a blemish, a dry skin, atopic dermatitis, dry scalp, an acne, a sore, a wart dry skin and stretch marks, uneven tone, blemishes, skin thickening, or thinning and a combination thereof.

In some embodiments, there is provided a method for improving the regeneration reversal, mitigation of the aging process, or healing of a human skin, the method comprising the step of applying the disclosed composition in an embodiment thereof on a region of a skin.

According to a non-limiting example, one method of treating the skin of a subject afflicted with symptoms of a skin condition related to aging, such as wrinkles, is via topical application of a safe amount of the topical composition of the invention.

In some embodiments, symptoms of a skin condition related to aging include, but are not limited to: wrinkles, reduction in skin smoothness, non-even skin tone, impaired skin complexion and the like.

In some embodiments, the frequency of topical application to the skin may vary widely, depending upon personal needs.

As a non-limiting example, the topical application of the composition of the invention may range from about once per week to about 10 times daily, or from about twice per week to about 4 times daily, or from about 3 times a week to about twice daily, or about once per day. Each possibility represents a separate embodiment of the present invention.

In some embodiments, the topical application would be over a period of from about one month to several years.

In some embodiments, the present invention provides a skin care treatment method for treating the cutaneous signs of aging, such as, but not limited to, wrinkles and skin atrophy and/or for protecting the skin against the harmful effects caused by ultraviolet (UV) radiation, the method comprising: topically applying to skin or skin appendages to be treated, the composition of the present invention.

In some embodiments there is provided a method for slowing the aging process of the human skin, reducing the signs of aging of the human skin or both, the method comprising applying to the skin of a subject afflicted with skin aging the topical composition of the invention.

In some embodiments, the amount of topical composition and frequency of treatment administered to a subject afflicted with skin aging or skin wrinkles varies widely depending upon the level of wrinkling already in existence in the subject, the rate of further wrinkle formation, and the level of regulation desired.

Slowing the aging process of the human skin and reducing the signs of aging of the human skin may include, but is not limited to, improvement of the skin tone, elasticity or contraction, reduction of wrinkles, removal of lines, combating the formation of skin wrinkles, promotion of skin firmness, reduction of skin sensitivity and irritability or any combination thereof. Each possibility represents a separate embodiment of the present invention.

In some embodiments, there is provided a method for protecting and/or improving the state of the skin of a subject and/or treating imperfections of the skin of a subject in need thereof, the method comprising topically administering the composition of the invention to the skin of a subject.

In some embodiments, protecting the skin of the subject relates to prevention of further worsening of existing skin conditions and/or arrest or slowing of existing skin conditions. Each possibility represents a separate embodiment of the present invention.

The present invention provides, in some embodiments, a method for preventing, retarding, arresting, or reversing atrophy in mammalian skin comprises the step of topically applying to the skin the topical composition of the invention. Each possibility represents a separate embodiment of the present invention.

In some embodiments, the present invention provides a topical composition for treating, preventing, retarding, arresting, or reversing skin atrophy in a subject in need thereof, the composition comprising the composition of the invention and an additional active ingredient and further comprising at least one dermatologically acceptable diluent, carrier, or excipient.

In some embodiments, the term "dermatologically acceptable diluent, carrier or excipient" refers to any diluent, carrier or excipient known in the art to be suitable for application to the skin. In some embodiments, the at least one dermatologically acceptable diluent, carrier or excipient is cosmetically suitable.

The term "cosmetically suitable" as used herein, relates to elements suitable to come into contact with the skin or human skin appendages without posing a risk of toxicity, intolerance, instability, allergic reaction, and the like.

In some embodiments, at least one dermatologically acceptable diluent, carrier or excipient is pharmaceutically acceptable. In some embodiments, the topical composition comprises at least one pharmaceutically acceptable carrier, diluent or excipient suitable for topical administration, preferably suitable for application to the skin.

Non-limiting examples of additional active ingredients that may be added to the composition of the invention, include, but are not limited to, retinoic acid and its derivatives, alpha and beta hydroxy acids (e.g., glycolic acid), hyaluronic acid, peptides, anti-oxidants, skin brightening compounds and the like. Each possibility represents a separate embodiment of the present invention.

As used herein, "atrophy" of skin means the thinning and/or general degradation of the dermis often characterized by a decrease in collagen and/or elastin as well as decreased number and size of fibroblast cells due to reduction in mitosis and access of cells in senescence. Skin atrophy may be a natural result of menopause, chronological aging and of photo-aging and often is an undesirable side effect resulting from corticosteroid treatment. Menopause may be physiological menopause or surgery- or treatment-induced menopause.

The present disclosure further provides, according to some embodiments, a method for treating, preventing, attenuating or ameliorating photo-aging or at least part of the symptoms thereof, comprising the step of topically administering the composition of the invention to the skin of a subject afflicted with photo-aging. Each possibility represents a separate embodiment of the present invention.

In some embodiments, the composition of the present invention is configured to be topically administered to a subject, for example, by direct application to the skin of a subject. Each possibility represents a separate embodiment of the present invention. In particular embodiments, the subject is a mammal, preferably a human.

As used herein, the term "photo-aging" includes, without limitation, aging of the skin associated with exposure to the sun or other ultraviolet energy sources. Symptoms of photo-aging include, for example, solar lentigo (age spots), solar keratoses dermatoheliosis or any combination thereof. Each possibility represents a separate embodiment of the present invention. The method of treating photo-aging includes, according to some embodiments, topically administering to an individual in need thereof a composition comprising the disclosed composition as defined above.

In some embodiments, the disclosed composition may be used against oxidative stress, for protection against toxic environmental influences, for protection against damage by UV light and for improving the functions of the dermal/epidermal junctions and to their use for improving the healing of wounds and preparations for treating alopecia, cellulitis or roseacea.

In some embodiments, the method of the invention may be performed either in vivo, specifically in a living organism, more specifically, in situ, within the tissue. In yet some further embodiments, the method of the invention may be performed in vitro, out of the body or injured tissue, for example, in a device, cell culture or any external system. Methods for evaluating epidermal cell viability and proliferation are known in the art.

In some embodiments, there is provided a method for protecting and/or improving the state of the skin of a subject and/or treating imperfections of the skin of a subject in need thereof, the method comprising topically administering the composition of the invention to the skin of a subject.

In some embodiments, there is provided a method for protecting the skin of a subject from skin conditions related to aging, comprising the step of administering the composition of the invention to the skin of the subject. In some embodiments, protecting the skin of the subject relates to prevention of further worsening of existing skin conditions related to aging and/or arrest or slowing of existing skin conditions related to aging or symptoms thereof.

In some embodiments, the plurality of the levan oligomers are present in an effective amount within the disclosed composition.

As used herein, the term "effective amount" relate to an amount of compound, a plurality of compounds (e.g., oligomers or polymers) or a composition that is capable of inhibiting, reducing, attenuating or treating at least part of the symptoms of a skin condition related to aging. In some embodiments, "effective amount" refers to "dermatologically effective amount".

In some embodiments, a dermatologically effective amount of a composition relates to an amount sufficient for inhibiting, reducing, attenuating or treating at least part of the symptoms of a skin condition related to aging upon topical administration of the composition to the skin of a subject in need thereof. Each possibility represents a separate embodiment of the present invention.

The specific dose of a compound administered according to this invention will, of course, be determined by the particular circumstances surrounding the case including, for example, the compound administered, the route of administration, the physiological state of the subject, and the severity of the pathological condition being treated.

In some embodiments, the disclosed composition is administered in several dosages over a prolonged period of time until a sufficient response has been achieved, such as, but not limited to attenuation or treatment of symptoms of a skin condition related to aging.

In some embodiments, promoting connective tissue reconstruction is affected in a skin condition or malady.

The phrase "injured tissue" as used herein refers to a deviation from healthy functional tissue. In the case of skin, a skin that is weaker, less elastic, and is more prone to injury than healthy skin. The structure of unhealthy or damaged skin is inferior to that of healthy skin (for example, the dermis and epidermis contain fewer cells and collagen). One purpose for treating unhealthy skin is to reduce further deterioration of skin and restore its function to normal or near-normal level.

In some embodiments, the composition of the invention is applied on a healthy skin.

The phrase "healthy tissue" as used herein refers to skin that is strong, elastic, smooth and plump. One purpose of treating healthy skin is to prevent deterioration of skin induced by aging or environmental stress including excessive sunlight and microbial infection.

The term "promoting" in respect to a connective tissue refers to the process of increasing the production of collagen by skin cells such as fibroblasts and keratinocytes, in a manner that allows tissue regeneration. Thus in some embodiments of the present invention, promoting refers to at least about 10%, at least about 20%, at least about 50%, or at least about 80% increase in tissue regeneration or at least about 10%, at least about 20%, at least about 50%, or at least about 80% arrest in tissue degradation.

Those of skill in the art will understand that various methodologies and assays can be used to assess the promotion of tissue regeneration, and similarly, various methodologies and assays may be used to assess the arrest of tissue degradation.

In some embodiments, an antimicrobial treatment against microorganism community is substantially not effected by the disclosed composition.

In some embodiments, by "not effected" it is meant that a reduction of at least 90%, at least 95%, or at least 99% of the level of microorganism cells is maintained upon applying an antimicrobial treatment, comparing to situation lacking the presence of the levan composition or a composition containing same.

In some embodiments, by "antimicrobial treatment" it is meant to refer to an antibacterial treatment such as antibiotic treatment. Non-limiting exemplary antibiotics are ampicillin, penicillin, and streptomycin In some embodiments, by "microorganism" it is meant to refer to bacterial cells. In some embodiments, by "bacterial cells" it is meant to refer to certain strains of Gram-positive or Gram-negative bacteria.

Non-limiting exemplary bacteria are *Staphylococcus epidermidis* and *Staphylococcus aureus*.

In some embodiments, the composition is formulated for oral administration.

In some embodiments, the disclosed composition is used as food additive, dietary supplement, feed additive or prebiotics. In some embodiments, the disclosed composition is for prebiotic use. In some embodiments, the disclosed composition is a feed additive. In some embodiments, the disclosed composition improves the feed conversion ratio (i.e. the weight of ingested feed relative to weight gain) of an animal. In some embodiments, the disclosed composition is a growth promoter. In some embodiments, the term "growth" as used herein refers to a gain in weight.

In some embodiments, the disclosed composition reduces the feed conversion ratio. In some embodiments, the disclosed composition increases weight gain of an animal.

The term "feed conversion" as used herein, refers to a ratio of feed consumption to body weight.

In some embodiments, a composition according to the present invention allow superior feed conversion efficiency and improved weight gain relative to un-supplemented diets. In some embodiments, a composition according to the present invention allow comparable feed conversion efficiency and improved weight gain relative to antibiotic supplements.

The term "prebiotic" as used herein is intended to encompass food ingredients beneficially affecting the host by selectively stimulating growth and/or activity of at least one gastro-intestinal bacteria, including probiotic bacteria.

The term "probiotic" as used herein refers to a live microbial food supplement that beneficially affects the host animal by improving its intestinal microbial balance.

The term "food or feed additive" as used herein refers to an essentially pure compound or a multi component composition intended for or suitable for being added to food or feed. In particular it is a substance that by its intended use is becoming a component of a food or feed product or affects any characteristics of a food or feed product.

The term "feed" as used herein refers to any compound or composition that are consumed by animals and contribute energy and/or nutrients to an animal's diet. Thus, unless specifically stated, the term "feed" should be taken to mean to include supplemental feed premixes etc. The feed may comprise different active ingredients. Exemplary animal feed ingredients include, for example, grains and grain products, other plant products such as hay, animal products, vitamin supplements, mineral supplements, and mixtures thereof.

In some embodiments, composition according to the present invention is supplemented to an animal at the beginning of each day. In some embodiments, composition according to the present invention is supplemented to an animal mixed with the food mixture (diet). In some embodiments, a composition is mixed with the animal diet in a concentration of 0.05% (w/w) to 1% (w/w). In some embodiments, a composition is mixed with the animal diet in a concentration of 0.1% (w/w) to 1% (w/w), 0.1% (w/w) to 0.7% (w/w), 0.1% (w/w) to 0.6% (w/w), 0.1% (w/w) to 0.5% (w/w), 0.1% (w/w) to 0.35% (w/w), 0.1% (w/w) to 0.3% (w/w), 0.05% (w/w) to 0.7% (w/w), 0.05% (w/w) to 0.9% (w/w), 0.05% (w/w) to 0.6% (w/w), or 0.05% (w/w) to 0.35% (w/w) including any range therebetween.

In some embodiments, feed additives according to the present invention are supplemented to the animal simultaneously with the diet. In some embodiments, feed additives according to the present invention are supplemented to the animal before and simultaneously with the diet. In some embodiments, feed additives according to the present invention are supplemented to the animal before the diet.

In some embodiments, compositions according to the present invention may also be provided to animals such as poultry, e.g., turkeys, geese, ducks, as well as swine, equine, bovine, ovine, caprine, canine and feline, as well as fish and crustaceans.

General

As used herein the term "about" refers to ±10%.

The terms "comprises", "comprising", "includes", "including", "having" and their conjugates mean "including but not limited to". The term "consisting of" means "including and limited to". The term "consisting essentially of"

means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms associated with a skin condition related to aging, such as, but not limited to, skin wrinkles, photo-aging and skin atrophy. In some embodiments, the term "treating" is further meant to include improvement of skin appearance and texture, improvement of skin hydration, healing, smoothing of the skin or any combination thereof. Each possibility represents a separate embodiment of the present invention. In some embodiments, the term "treating" refers to at least partial smoothing of existing wrinkles and/or slowing of deepening of existing wrinkles and/or preventing formation of new wrinkles. Each possibility represents a separate embodiment of the present invention. In some embodiments, the term "treating" refers to amelioration, arrest or prevention of skin thinning and/or skin degradation. Each possibility represents a separate embodiment of the present invention.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Levan Samples Characterization

A. Levan Oligomers Characterization

MALDI-TOF

This method is suitable for small molecules up to 10,000 grams per mole. One example was tested.

Various samples were obtained by various processes using the corresponding enzyme (Table 1A):

TABLE 1A

| number | Total solids g/kg | levan g/kg | glucose g/kg | sucrose g/kg | fructose g/kg |
|---|---|---|---|---|---|
| A2845 | 610 | 322 | 219 | 34.8 | 24.0 |
| A2846 | 610 | 330 | 204 | 45.0 | 19.2 |
| A2847 | 610 | 357 | 204 | 24.0 | 15.0 |
| A2848 | 610 | 324 | 209 | 51 | 16.8 |

Samples 2845-8 contain about 70% to 98% levan oligomers (having 3-4 units) and about 30% to 2% levan polymers.

The below results characterize the oligomers in the samples.

Figure 1B:
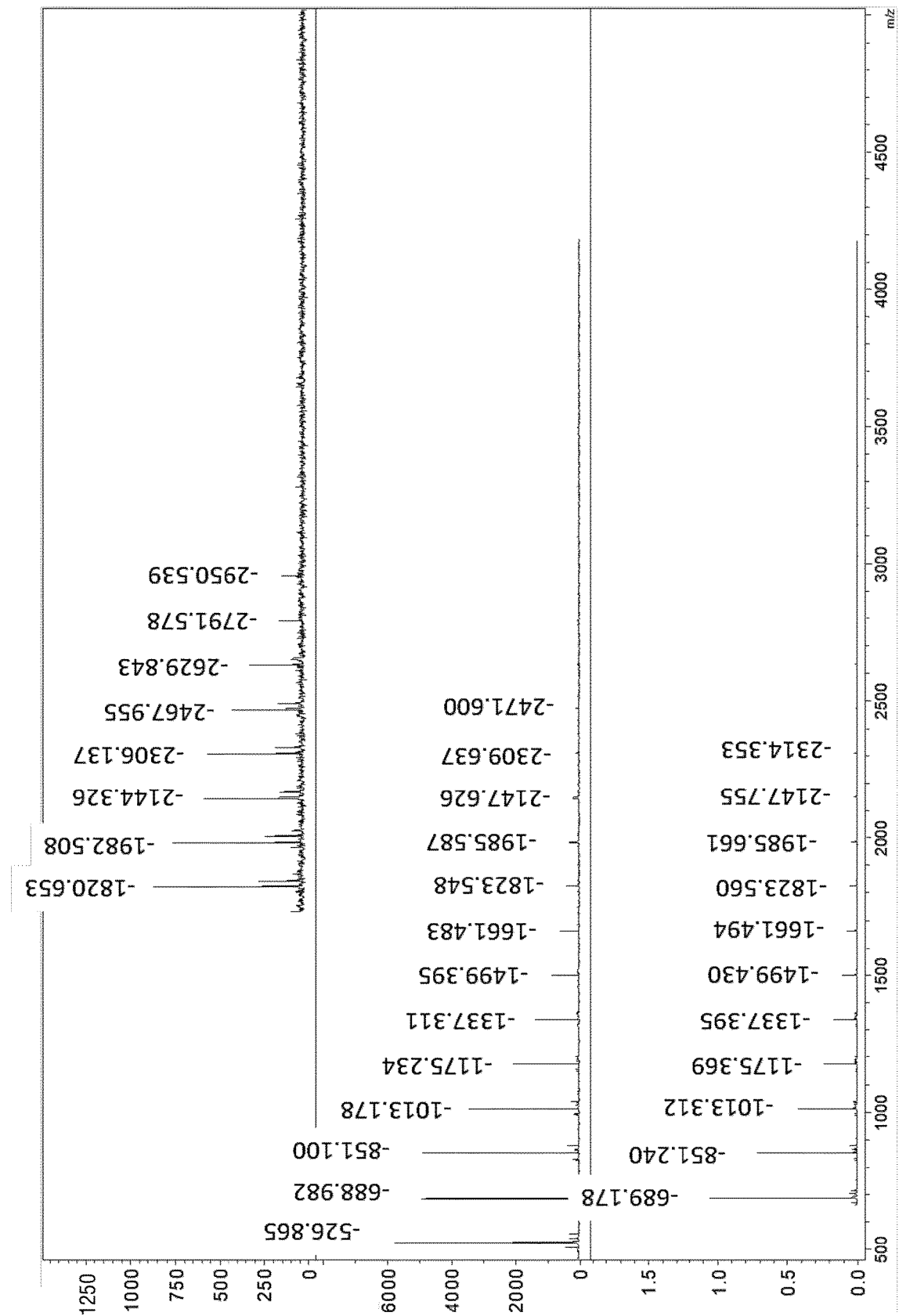

The graphs in FIGS. 1A-1B present an exemplary sequence of peaks between 527-1157 g/mole for Samples 2845 and 2847, respectively (with differences of 162 g/mol=fructose molecule without water molecule), total 5 peaks. Accordingly, there is mainly a molecule with 3 monomers (Kestose).

Dionex Anion Chromatography

Figure 2:
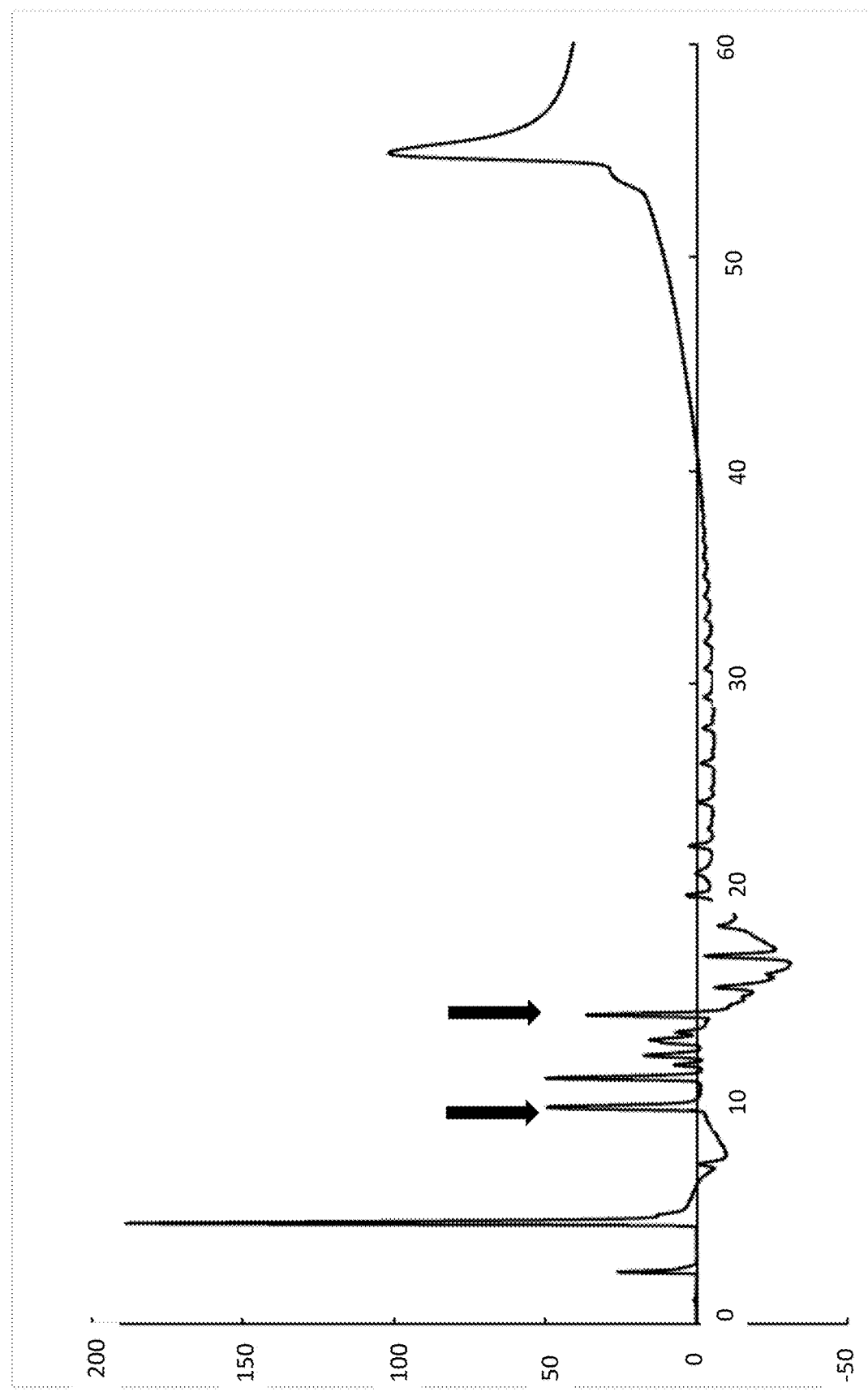
FIG. 2 presents typical graph obtained by Dionex anion chromatograph; the relevant peaks were assigned to Kestose (mainly, about 90%; left arrow) and Nystose (right arrow)

In a typical graph (see FIG. 2) the relevant peaks were assigned to Kestose (mainly, about 90%) and Nystose.

B. Levan Polymer Characterization

GPC-MALLS

The instrument tests: light dispersion of molecules above 10,000 g/mole and index refraction of all fractions.

The samples were tested, and Table 1B below summarizes the results for the levan polymers in the tested examples.

TABLE 1B

|  | 2845-1 | 2845-2 | 2846-1 | 2846-2 |
|---|---|---|---|---|
| Injected mass (g) | 2.4/1,000 | 2.4/1,000 | 1.74/1,000 | 1.74/1,000 |
| Calculated mass (g) | 1.65/10,000 | 1.55/10,000 | 1.36/10,000 | 1.39/10,000 |
| Polydispersity ($M_w/M_n$) | 7.48 | 7.8 | 6.0 | 8.1 |
| $M_w$ (g/mol) | 5,000,000 | 5,220,000 | 9,220,000 | 9,290,000 |

AF4-MALS

Five levan samples with different compositions were characterized by asymmetrical flow field-flow fractionation (AF4) coupled with multiangle light scattering and differential refractive index detection (AF4-MALS/dRI).

Table 2 shows the composition of the different levan samples used.

TABLE 2

| Sample designation | Sample description |
|---|---|
| 1 | Powder- Mean Molecular Weight: 300,000-96.9% |
| 2 | Powder- Mean Molecular Weight: 800,000-95.5% |
| 3 | Powder- Mean Molecular Weight: 800,000-94% + 4% sugar |
| 4 | Powder- pure levan (standard from Sigma, by fermentation) |
| 5 (the disclosed composition) | Liquid- composition: 32% levan (about 80% oligomers- less than 2,000 dalton; 20%- probably between 1-10 million Dalton), 32% sugars (mainly glucose), 0.4% sodium, 1% citrate, 0.1% potassium sorbate (levan LMW) |

In exemplary embodiments, the samples were evaluated according to the following characteristics: molar mass (MM), apparent density across the distribution, and relative amounts of different components present in the samples. Table 3 shows the average values of MM, measured for each sample.

TABLE 3

| Sample | MM ($\times 10^6$ Da) |
|---|---|
| 1 | 0.150 |
| 2 | 41.13 |
| 3 | 21.8 |
| 4 | 42.9 |
| 5 | 0.733 |

Comparison of Different Samples

Samples 2 and 3 have populations with distinctly different structures ($r_{rms}/r_h$) ($r_{rms}$: root mean square radius). The longer retention time of sample 2 indicates that this sample has larger $r_h$ compared to sample 3 ($r_h$ is derived from AF4 retention times while $r_{rms}$ is derived from MALS data).

Sample 2 has a similar average MM as sample 4.

Figure 3:
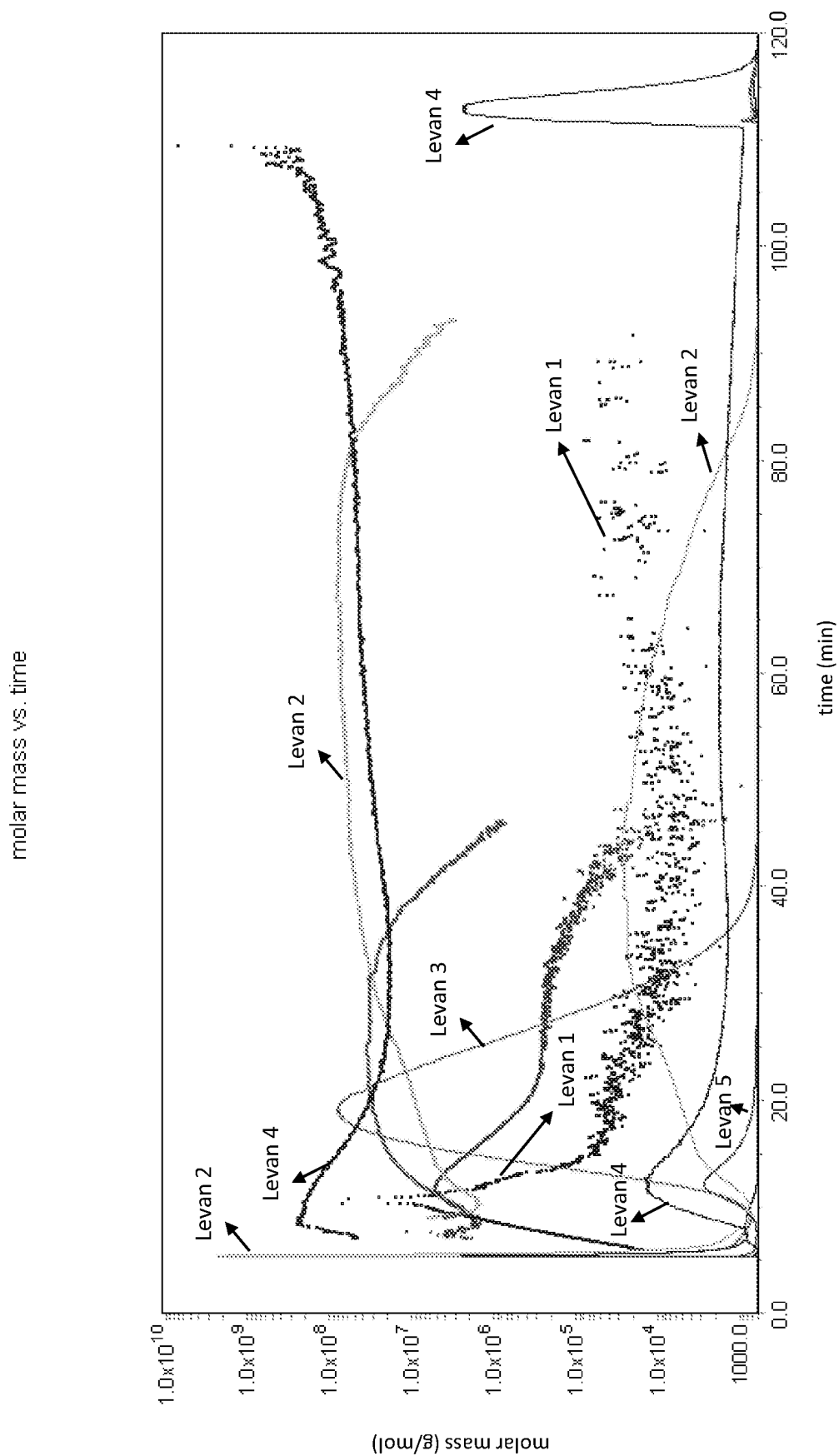
FIG. 3 presents a graph showing the comparison of the molar mass (MM) distributions of the five polymeric levan samples.

FIG. 3 shows the cooperation of MM distributions of Samples 1-5 across the elution profiles of the levan samples.

Interestingly, the samples show a down turn in the MM at longer retention times. This indicates a structure/density change in the samples, as larger sized samples (or samples that occupy a larger volume) have lower molecular weights. These results could indicate levan aggregation.

Relative Amounts of Sample Components

The calculation of the relative amounts of different sample components was not possible due to the weak dRI signal.

The weak dRI signal resulted from the significant dilution of the sample over the extremely long retention times.

Figure 4:
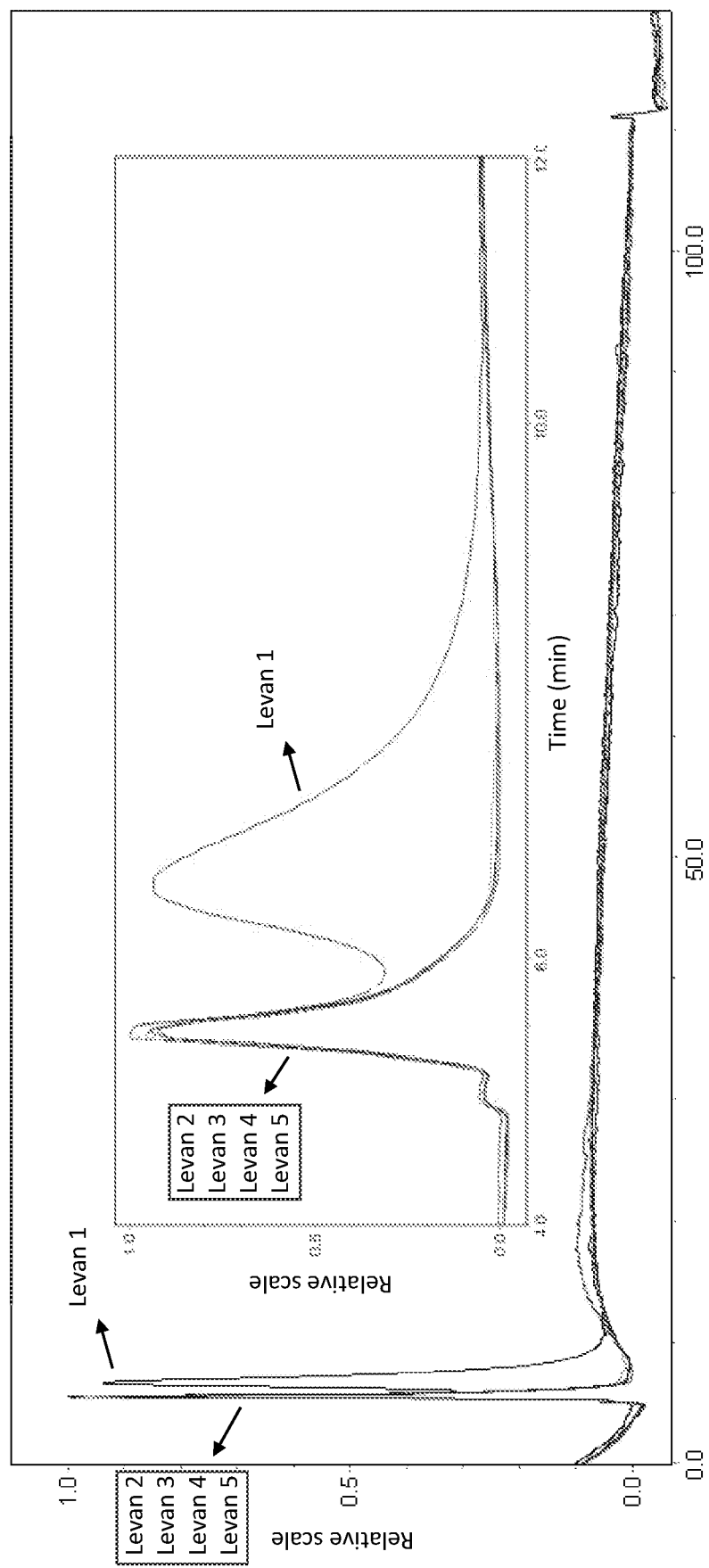
FIG. 4 presents a graph showing the comparison of the differential refractive index (dRI) fractograms of the four levan samples (1-4) as described below, and the disclosed sample (sample 5) (inset graph shows enlarge view of the 4 to 12 min scale)

The dRI fractograms for each sample are presented in the comparative graphs in FIG. 4.

As shown in FIG. 4, the sharp peak at 5.5 minutes corresponds to the void peak and represents the components of the sample that are not retained in the AF4.

All levan samples showed a void peak with similar intensity.

Levan sample 5 which has a high relative concentration of oligomers and sugars that are not retained in the AF4 and could lead to a larger void peak, showed a similar void peak to samples 1 to 4.

All samples (1 to 5) had similar dRI traces beyond 10 minutes.

The fractogram of Sample 1 shows an intense peak at approximately 6.8 minutes which is reflective of a relatively high concentration of lower molar mass components (as shown in the zoom-in of the dRI fractogram in FIG. 6).

Table 2 and FIG. 3 show that the levan of Sample 1 has a much lower molar mass and a much smaller size which is reflected in the dRI fractogram as well as the MALS fractograms.

Structure/Apparent Density Distributions

FIGS. 5-9 show the structure factor $r_{ho}$ ($r_{rms}/r_h$) and apparent relative density distributions for each sample.

The apparent relative density is obtained by normalizing all density calculations (MM/size) to the density of the first data point.

Levan samples 1 and 5, which have lower MM and smaller size distributions, appear to have more particle-like characteristics in solution, while levan samples 2, 3 and 4 with large sizes and high molecular weights, behave more like polymer networks or gels.

Without being bound to any particular theory, this is consistent with the concept of high molecular weight levan being a supramolecular assembly consisting of many smaller dense individual levan oligomers aggregated together.

These results are in agreement with the fact that levan samples 1 and 5 were easily solubilized at 2 mg/mL and yielded clear solutions while the high molar mass levan samples 2, 3 and 4 were turbid at 2 mg/mL.

Figure 5:
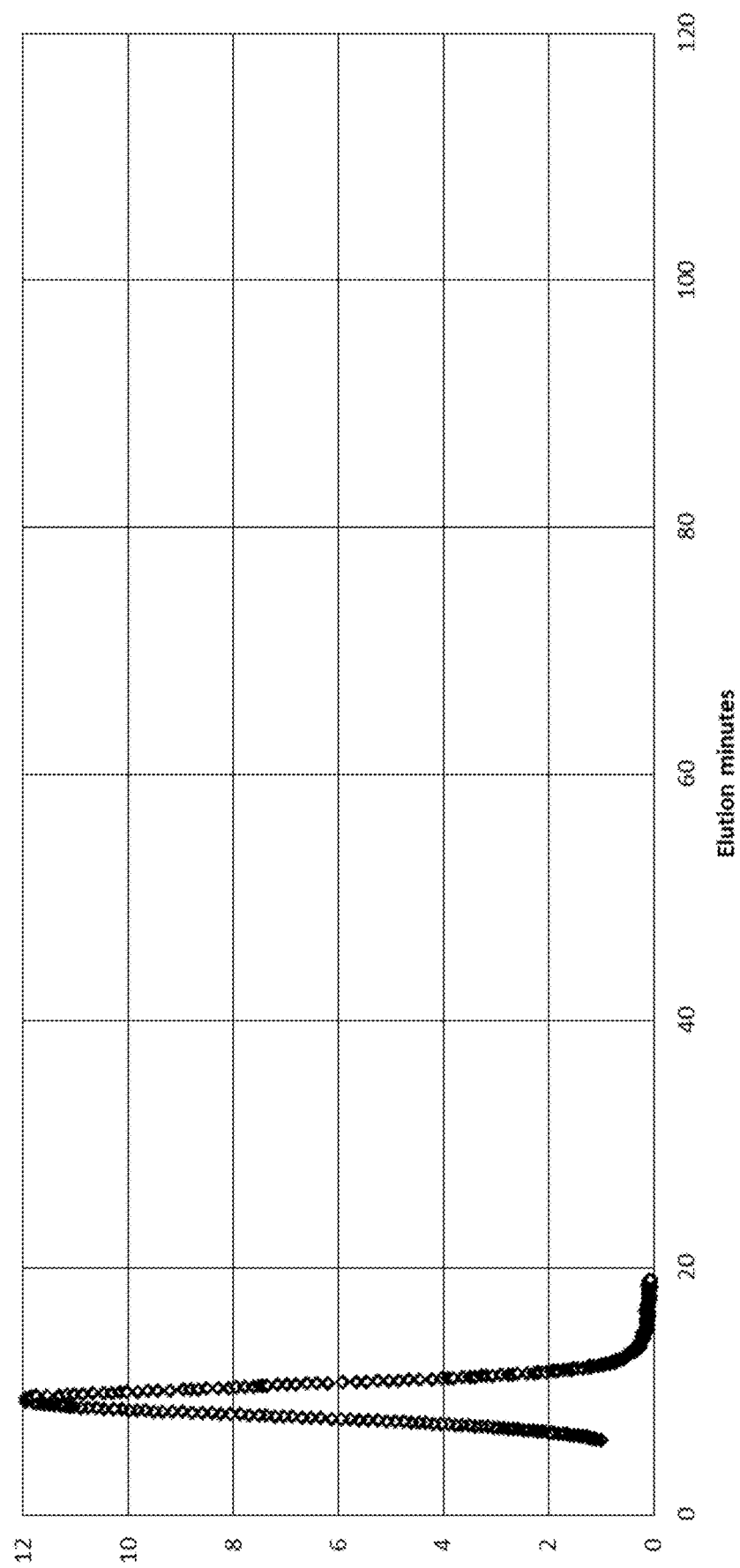
FIG. 5 presents a graph showing the apparent relative density plot for levan sample 1.

The apparent density plot for levan sample 1 shows a small dense structure (FIG. 5).

Figure 6A:
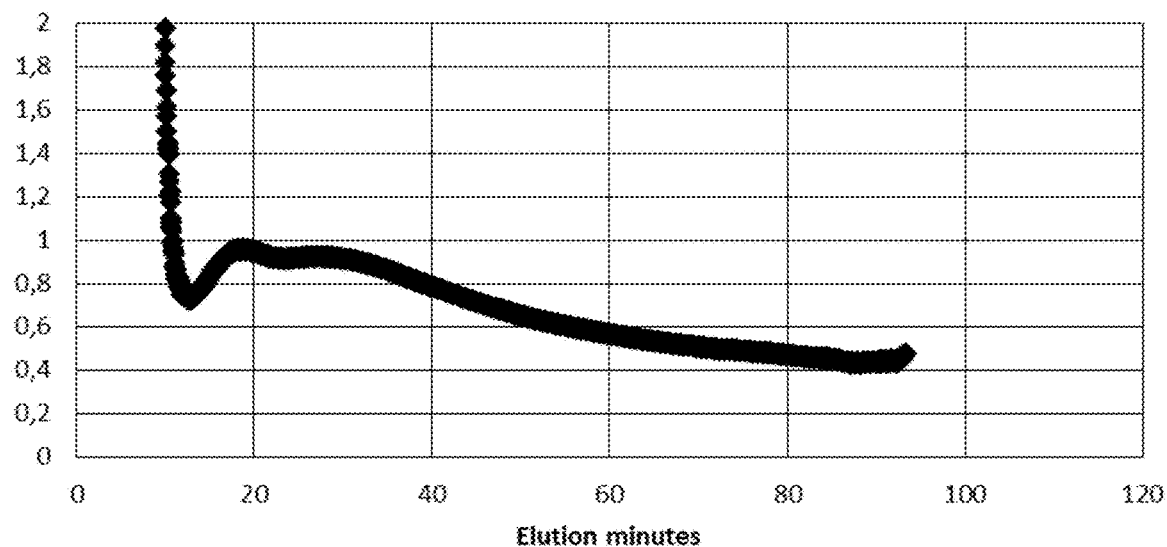
FIGS. 6A-6B present graphs showing the structure distribution and the apparent relative density plots for levan sample 2, respectively.
Figure 6B:
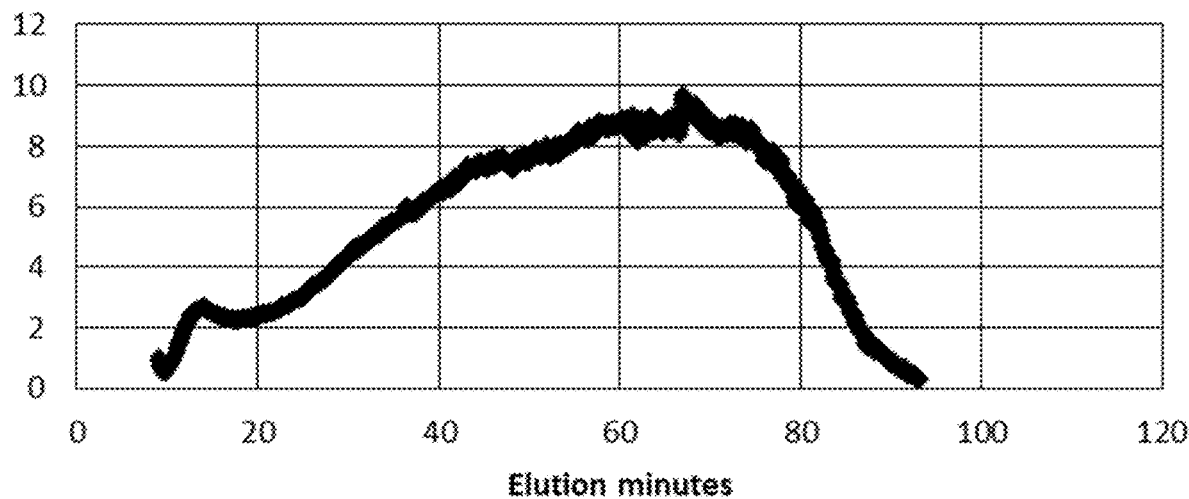

The apparent density plot for sample 2 shows an increase in relative density for larger sized levan molecules while the rho distribution shows a trend from spherical particles to branched networked polymers (FIGS. 6A-6B).

Figure 7A:
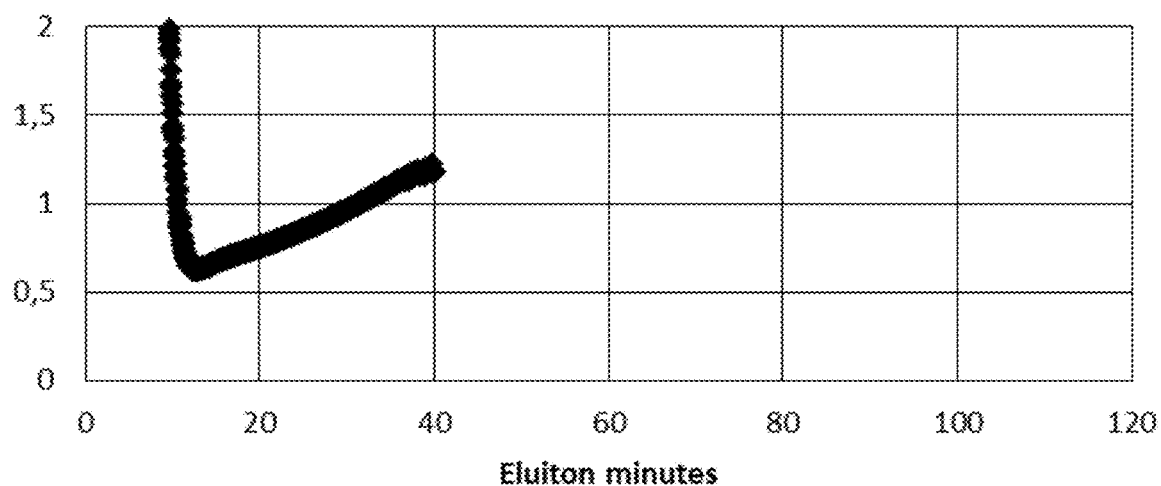
FIGS. 7A-7B present graphs showing the structure distribution and the apparent relative density plots for levan sample 3, respectively.
Figure 7B:
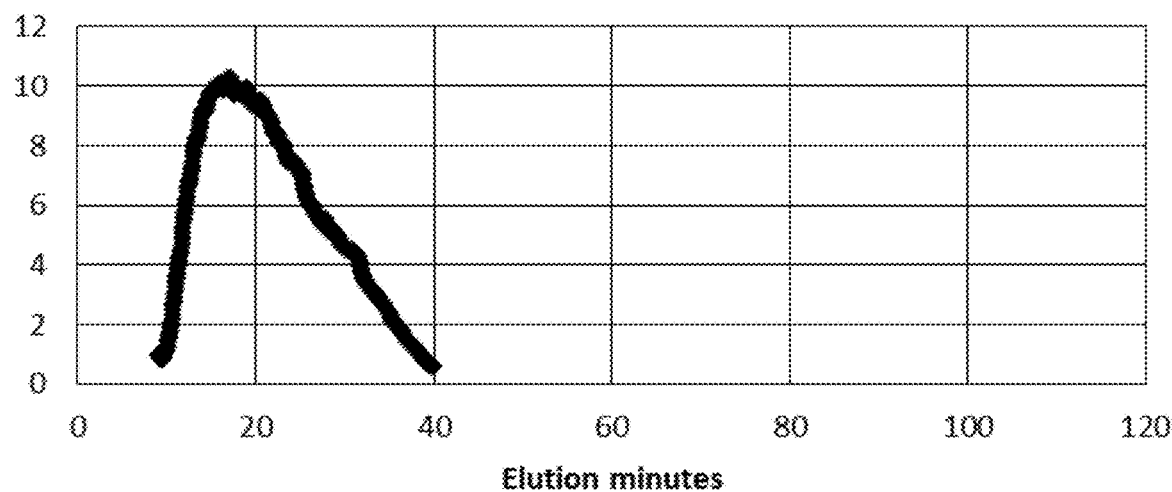

The apparent density and structure distribution plots for levan sample 3 are shown in FIGS. 7A-7B.

Figure 8A:
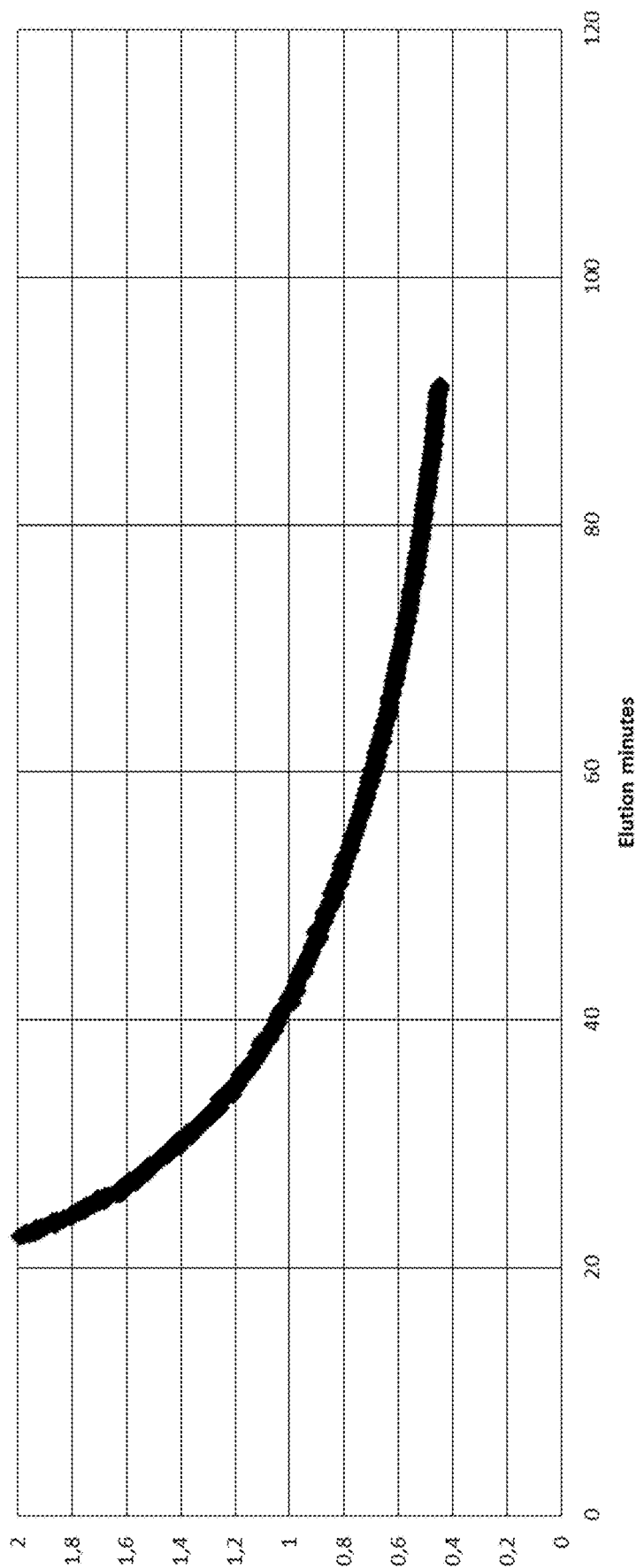
FIGS. 8A-8B present graphs showing the structure distribution and the apparent relative density plots for levan sample 4, respectively.
Figure 8B:
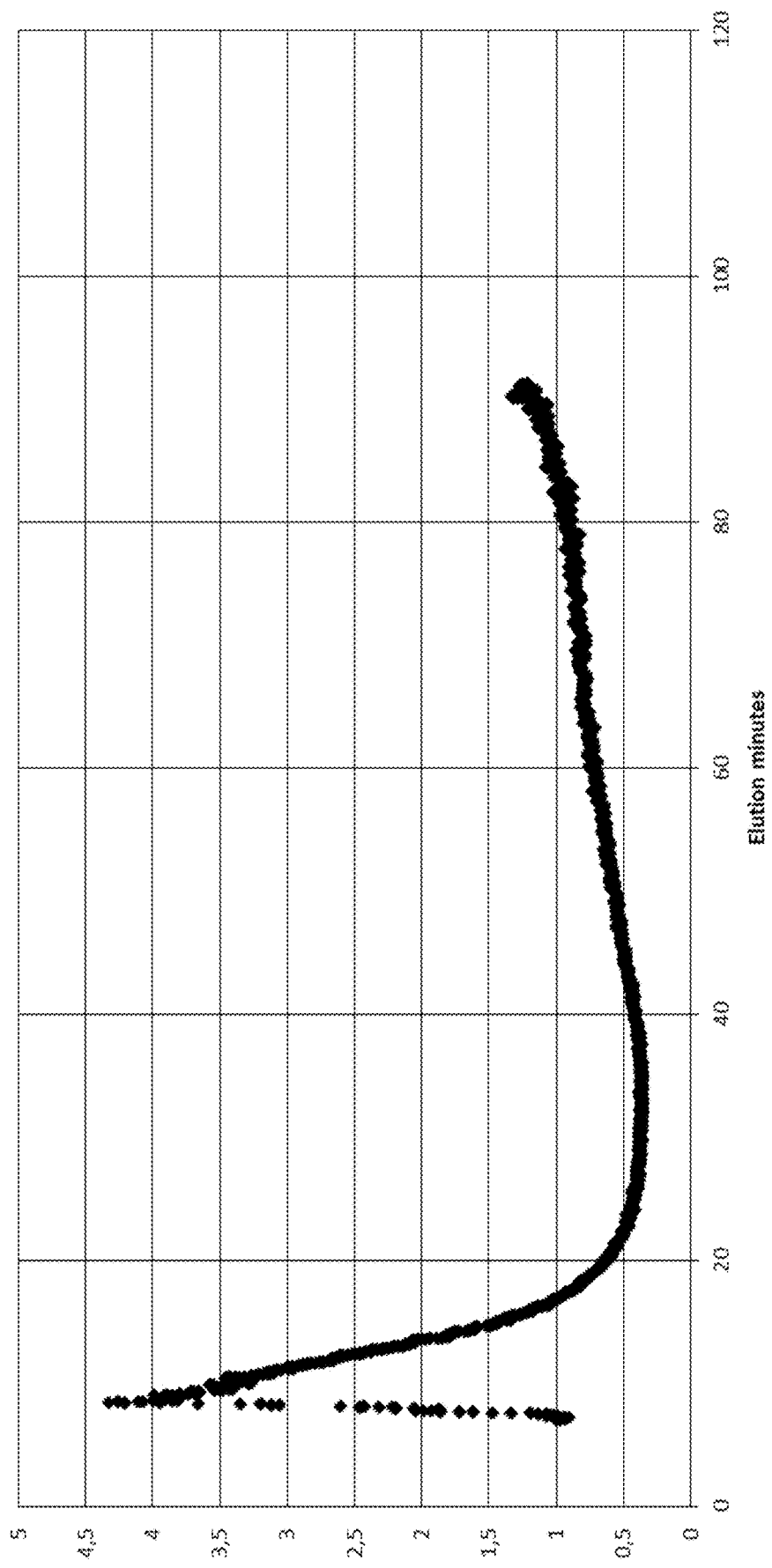

The apparent density and structure distribution plots for levan sample 4 are shown in FIGS. 8A-8B.

After 20 minutes elution time, the structure of levan sample 4 approaches a highly networked polymer while the apparent density increases only slightly, which can indicate supramolecular structures.

Figure 9A:
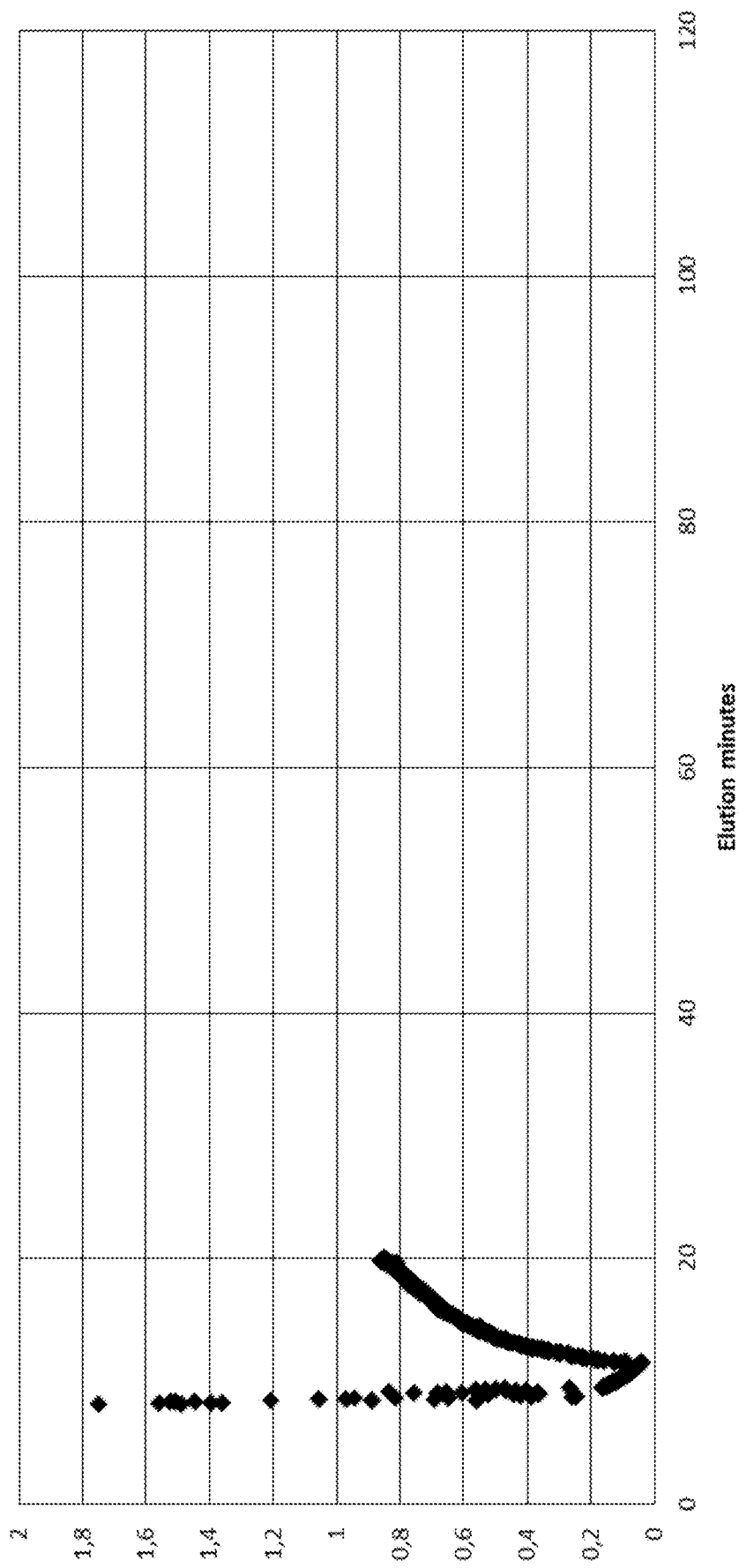
FIGS. 9A-9B present graphs showing the structure distribution and the apparent relative density plots for levan sample 5, respectively.
Figure 9B:
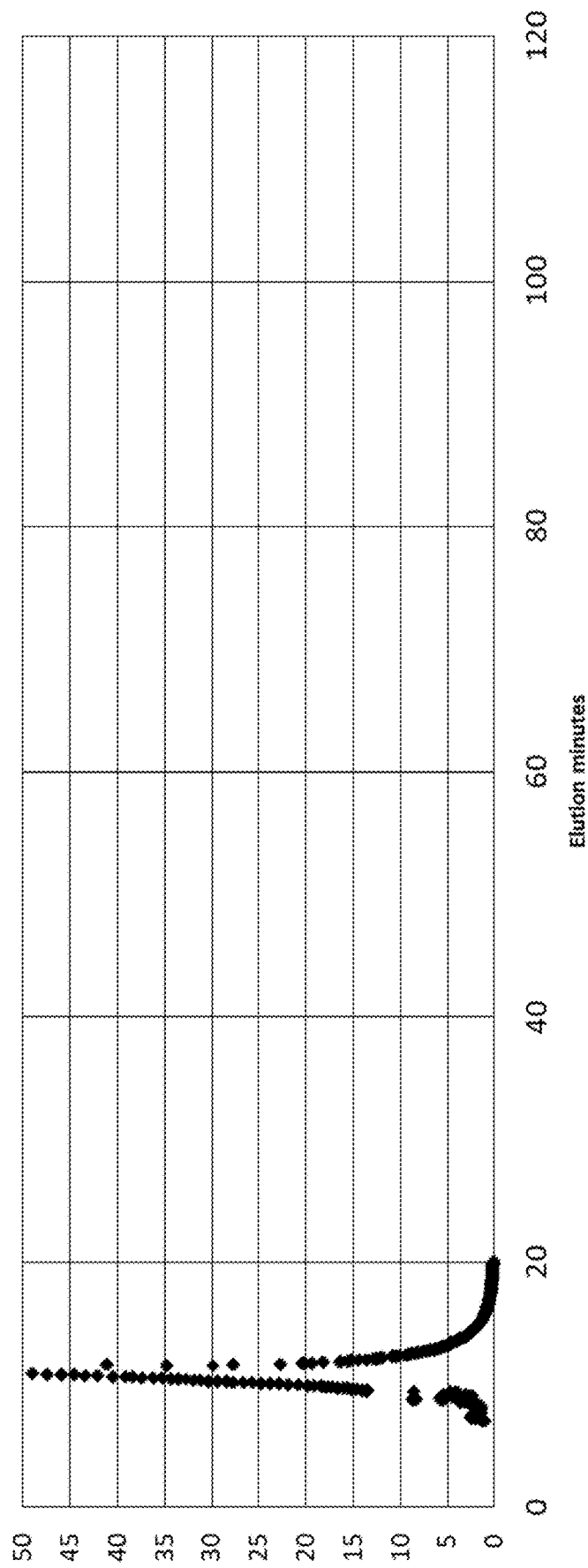

As shown in FIGS. 9A-9B, the apparent density and structure distribution plots for levan sample 5 indicates that this sample consists of a small dense population.

Example 2

Skin Rejuvenation Evaluation

Materials and Methods

The material list is presented in Table 4.

TABLE 4

| No./Name | Manufacturer/ Supplier | Cat No./Lot No | Physical State/ storage conditions | Expire date | Name in the report |
|---|---|---|---|---|---|
| Test items | | | | | |
| 1. Baseline solution- for 8% | Gan-Shmuel Gan-Shmuel | N/A 4.10.17 | Liquid 2-8° C. | N/A | Vehicle |
| 2. Competitor Levan (commercial reference)- Levan RB 8% | Gan-Shmuel Gan-Shmuel | N/A 4.10.17 | Liquid 2-8° C. | N/A | C.R. |
| 3. Levan 28- 30-8% | Gan-Shmuel Gan-Shmuel | N/A 4.10.17 | Liquid 2-8° C. | N/A | Test item |
| 4. HA with Baseline 8% | Gan-Shmuel Gan-Shmuel | N/A 4.10.17 | Liquid 2-8° C. | N/A | Hyaluronic acid |
| Skin culture medium | | | | | |
| 5. DMEM | Biological industries Biological industries | 01-052-1A 1728619 | Liquid 2-8° C. | 07.18 | DMEM |
| 6. Penicillin- streptomycin solution | Biological industries Biological industries | Frozen 1628553 | Liquid (−25)- (−15)° C. | 01.18 | Pen-Strep |
| Other chemicals | | | | | |
| 7. PBS | Biological industries Biological industries | 02-023-1A 1621025 | Liquid RT | 12.18 | PBS |
| 8. MTT | Sigma- Aldrich Sigma- Aldrich | M5655-1G MKBX6716V | powder 2-8° C. | N/A | MTT |
| 15. Epidermal Growth Factor | Invitrogen Rhenium | PHG0311 1380077A | Powder 2-8° C. | 3.18 | EGF |
| Bio-markers quantification | | | | | |
| 16. BrdU | Enzo Abeam | Ab126556 6R299242-1 | N/A 2-8° C. | 9.18 | BrdU |

Dexamethasone—(10 μM) Stock (10 mM): 19.6 mg of Dexamethasone was reconstituted in 5 ml DMSO. Then, the stock was diluted 1:1000 in culture medium to reach a final concentration of 10 μM.

EGF (10 ng/ml)—Stock (200 μg/ml): 100 μg of lyophilized epidermal growth factor (EGF) was reconstituted in 0.5 mL PBS, aliquoted and stored at −20° C. The stock was then diluted in a stepwise manner 1:20 and then 1:1000 in skin culture medium supplemented with 10% FCS to reach a final concentration of 10 ng/ml.

MTT stock (10×)—3-(4,5-Dimethylthiazol-2-yl)-2,5-Diphenyltetrazolium Bromide (MTT) powder was dissolved in PBS to prepare a 5 mg/ml stock solution. The stock was filtered through 0.2 micron filter, aliquoted and stored at −20° C. At the day of assay, the stock was diluted 1:10 in PBS.

Test Items—The Test items (including hyaluronic acid) were received sterile and ready to use. The Test items were stored at 4° C. until used.

Disposal of Materials—The disposal of samples was carried out by the test facility.

General equipment—Plate Shaker $CO_2$; Incubator; Biological Hood; Type II Plate reader.

All formulations were prepared under sterile conditions.

Skin Culture Medium—Dulbecco Minimal Essential Medium (DMEM) was supplemented with 100 U/ml penicillin and 100 μg/ml streptomycin, filtered.

LPS (5 μg/ml)—Stock (5 mg/ml): 50 mg of lyophilized lipopolysaccharide (LPS) were reconstituted in 10 ml phosphate saline buffer (PBS), aliquoted and stored at −20° C. The stock was diluted 1:1000 in culture medium to reach a final concentration of 5 μg/ml.

Skin Preparation

The human skin organ culture was obtained from a healthy patient undergoing plastic surgery (female, 42 y.o.). The study was initiated at the day of surgery.

Fixed size skin explant pieces (0.64 cm$^2$) were cut from the skin tissue, using a designated press apparatus.

The skin pieces were prepared and maintained in air liquid interphase; the explants were laid in 6-well culture plates containing skin culture medium (Dulbecco Minimal Essential Medium (DMEM) supplemented with 100 U/ml penicillin and 100 µg/ml streptomycin), dermal side down in the medium and epidermis phasing up. The pieces were left to recover at 37° C. with 5% $CO_2$ overnight.

After recovery, the skin pieces were treated as follows.

Skin Rejuvenation Properties Evaluation

In exemplary embodiments, two different parameters were examined; thus, two sets of each test group were prepared.

The examination has been performed concomitantly.

The assay was carried out in triplicates.

Both the commercial reference (C.R.) and hyaluronic acid were supplemented with a vehicle (which contains sucrose, hexoses, buffers and preservative) to exclude possible impact of non-Levan compounds.

After recovery, the skin pieces were treated without or with six concentrations of the Test item and the C.R (Table 5, Groups 6-16) by topical application (3 µl).

The following control groups were also included in this study: Naïve group (Group 1), Vehicle group (mock treatment—hexose, Group 2), and positive control groups for viability and proliferation (10% SDS, Group 3 and 10 ng/ml EGF, Group 4, respectively). Hyaluronic acid was evaluated in this system (0.2%, Group 5). Additional blank control group was included (media w/o skins or assay reagents, Group 18).

The pieces were incubated at 37° C. with 5% $CO_2$ under humidified atmosphere for 48 hr. At the end of incubation, the epidermis of one set of the test groups was separated from the dermis. The epidermal viability was evaluated by MTT, according to standard operating procedure (SOP). A blank control was subtracted from the measurements. Concomitantly, the epidermal turnover rate was determined on the second set of test groups by BrdU assay according to the kit's manufacturer instructions.

Briefly, during the final 2 hours of culture, epidermis was peeled and BrdU was added to each well.

The epidermis samples were fixed, permeabilized and DNA denatured by the kit's buffers.

BrdU monoclonal antibody was pipetted into the wells and allowed to bind for one hour.

Colorimetric evaluation of the turnover rate was recorded by Enzyme-Linked Immunosorbent Assay (ELISA) reader.

The spent media from all test groups was centrifuged at 1,500×g for 5 min to remove particulates. Clear supernatants were frozen at −80° C. until analyzed.

Table 5 summarizes the results of skin rejuvenation.

TABLE 5

| Group | Description | Concentration |
|---|---|---|
| 1. | Control naïve tissue | n/a |
| 2. | Vehicle control | n/a |
| 3. | Positive control (viability) | 10% SDS |
| 4. | Positive control (proliferation) | 10 ng/ml EGF |
| 5. | Hyaluronic acid | 0.2% |
| 6. | Test item | 0.01% |
| 7. | | 0.1% |
| 8. | | 0.5% |
| 9. | | 1% |
| 10. | | 5% |
| 11. | | 8% |
| 12. | C.R. | 0.01% |
| 13. | (commercial reference) | 0.1% |
| 14. | | 0.5% |
| 15. | | 1% |
| 16. | | 5% |
| 17. | | 8% |
| 18. | Blank | n/a |

Skin Rejuvenation

The skin rejuvenation properties of the Test Item and C.R were examined by skin viability and turnover assays.

Figure 10A:
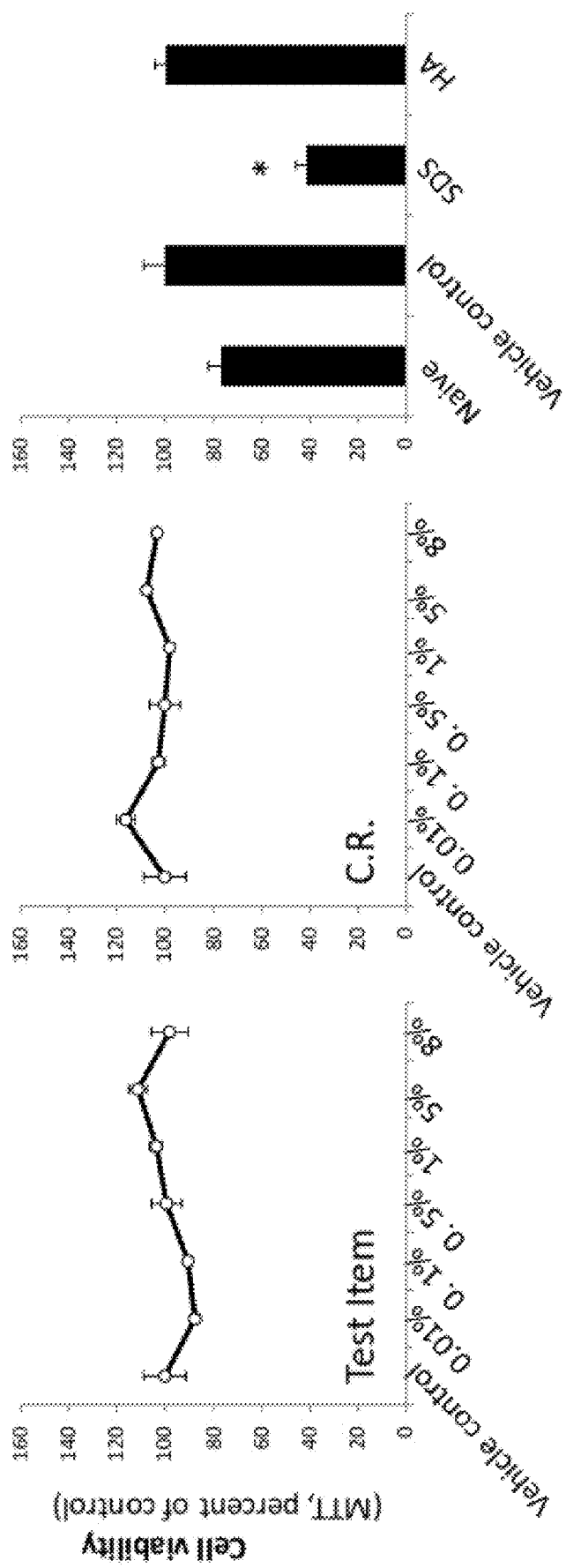
FIGS. 10A-10B present graphs showing the results of the skin rejuvenation evaluation: the viability (FIG. 10A) and turnover rate (FIG. 10B) of the test groups were examined by the MTT (left and middle panels: Tested Item and control reference (C.R.), respectively; right panels are bar graphs showing the results of the treatment with additional tested groups) and BrdU method, respectively, as described in Example 2.

Neither the Test Item nor the C.R reduced skin viability, which was measured by the MTT assay (FIG. 10A, left and middle panels). In contrast, treatment with 10% SDS, reduced skin viability as expected, FIG. 10A, right panel.

Concomitantly, the turnover rates of the Test Groups were evaluated by using a commercial bromodeoxyuridine (BrdU) proliferation kit.

Figure 10B:
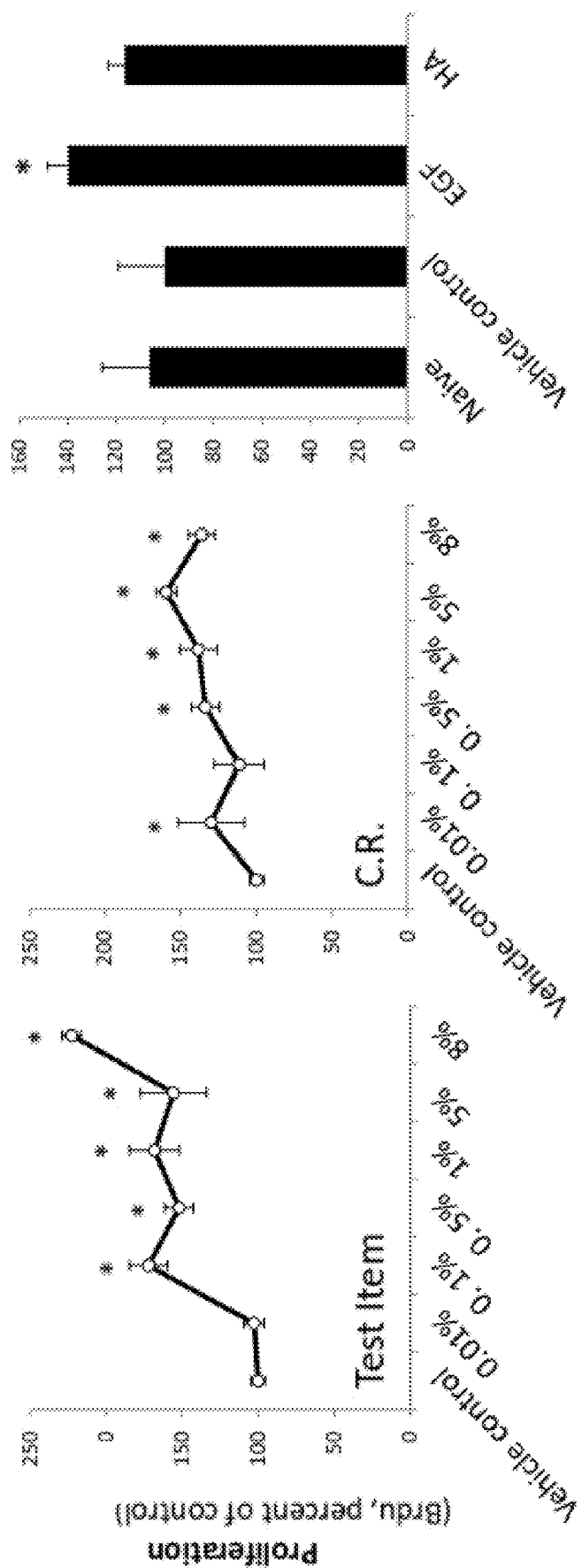
Figure 11A:
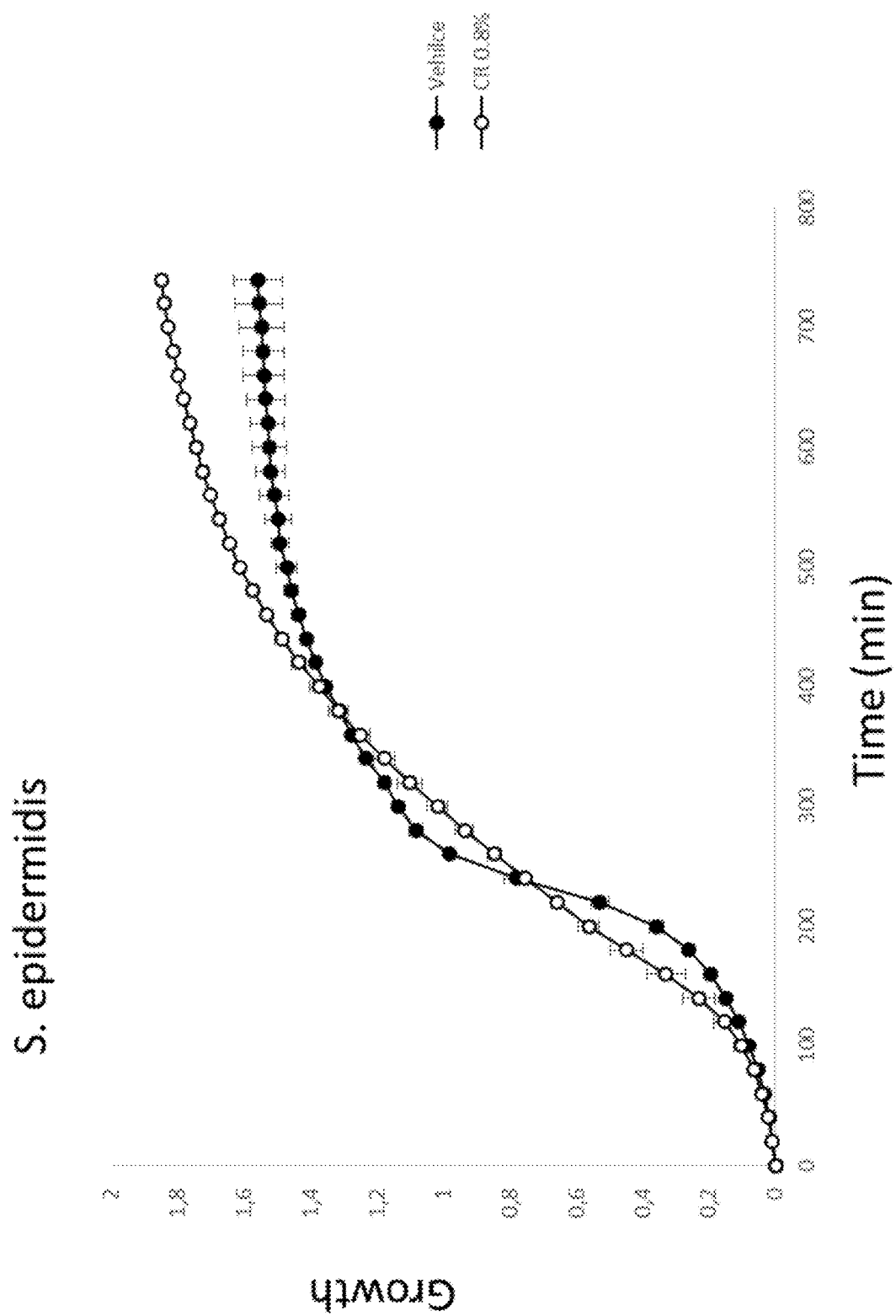
FIGS. 11A-11M present graphs showing the impact of the test items on bacterial growth: the bacterial cultures were incubated w/o or with the test items, as described in the Example section below: the growth of *S. epidermidis* growth was assessed kinetically. Data are presented as O.D. (arbitrary units). Mean±SEM; n=3. p<0.05 for differences from the naïve placebo control group.
Figure 11B:
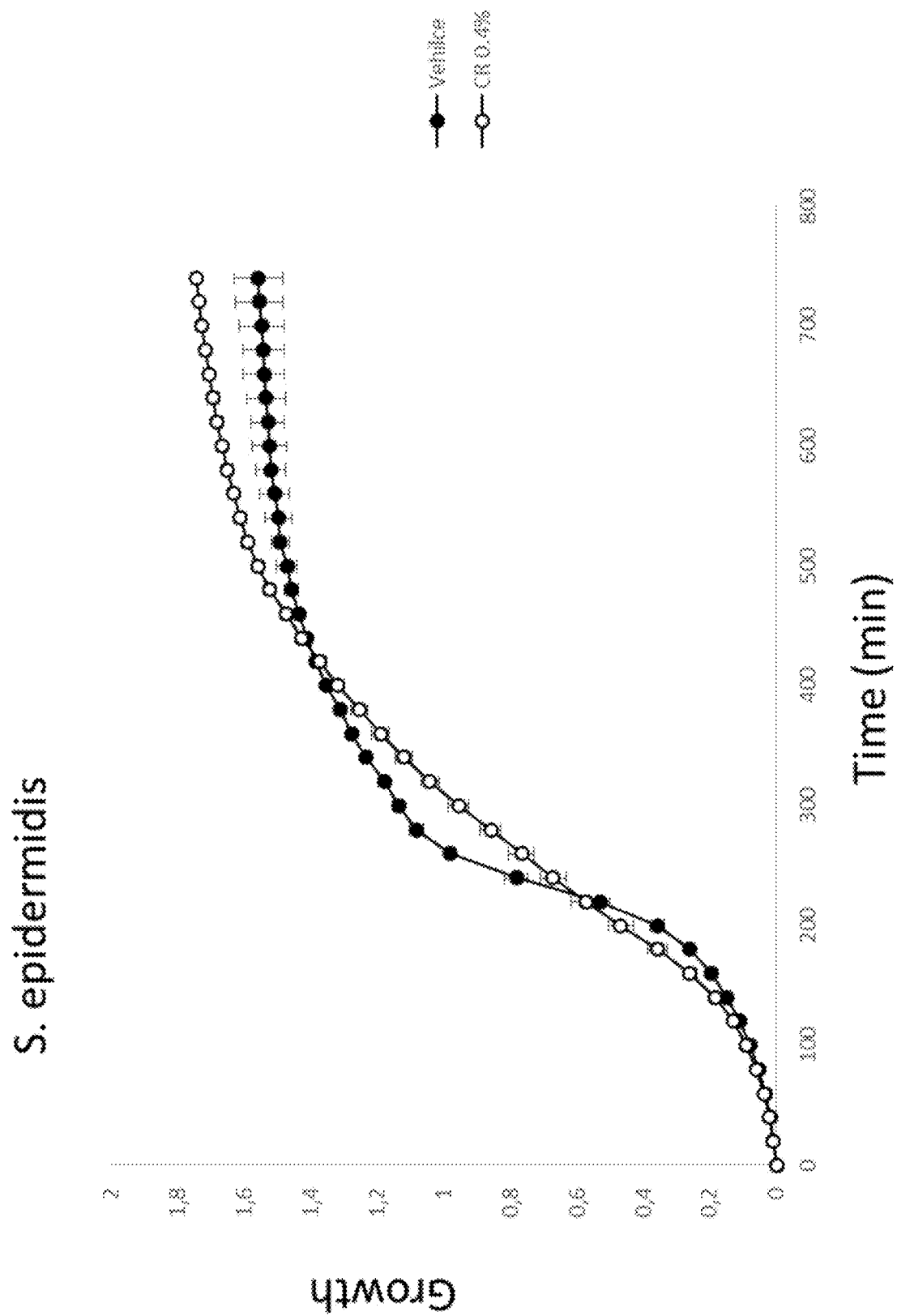
Figure 11C:
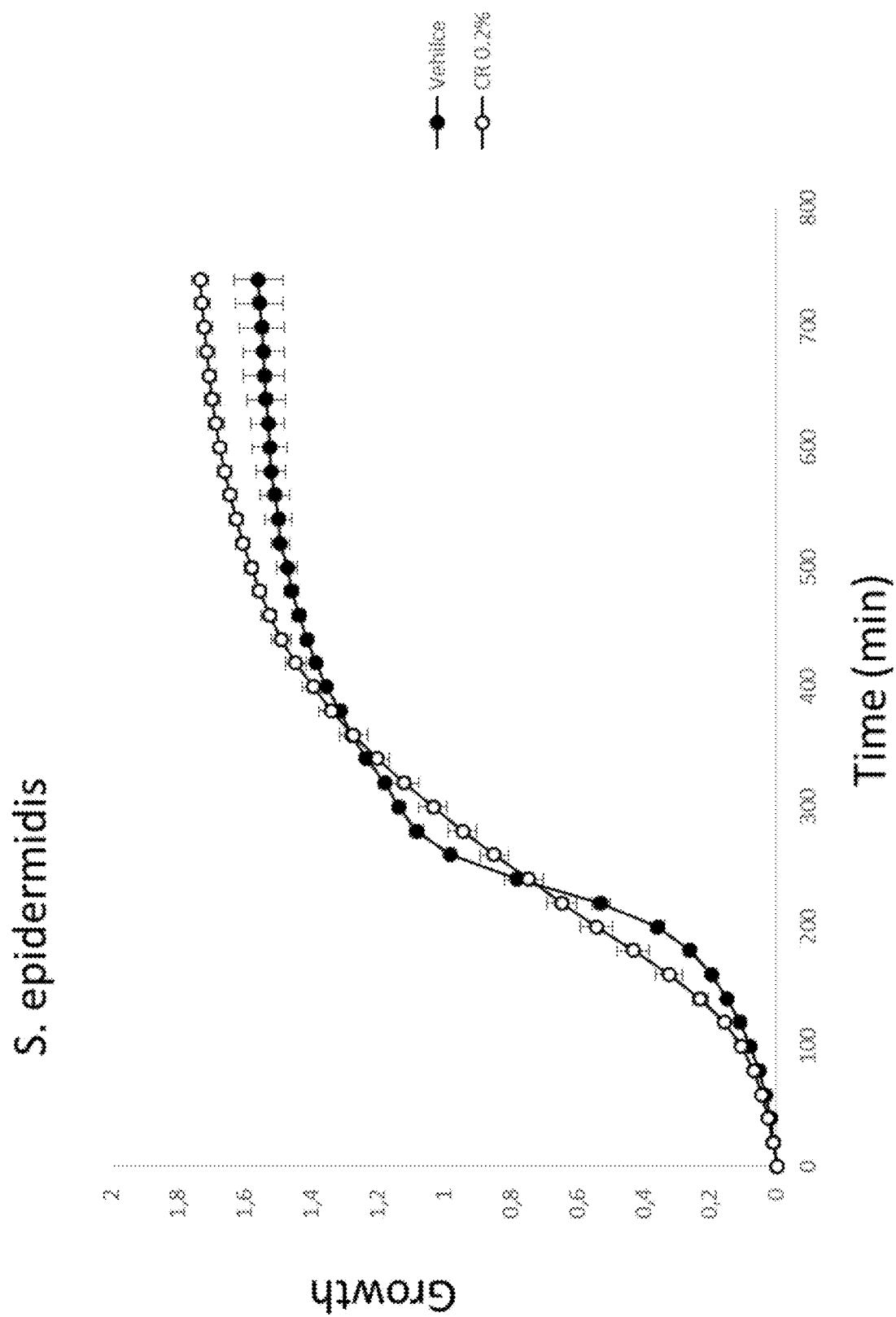
Figure 11D:
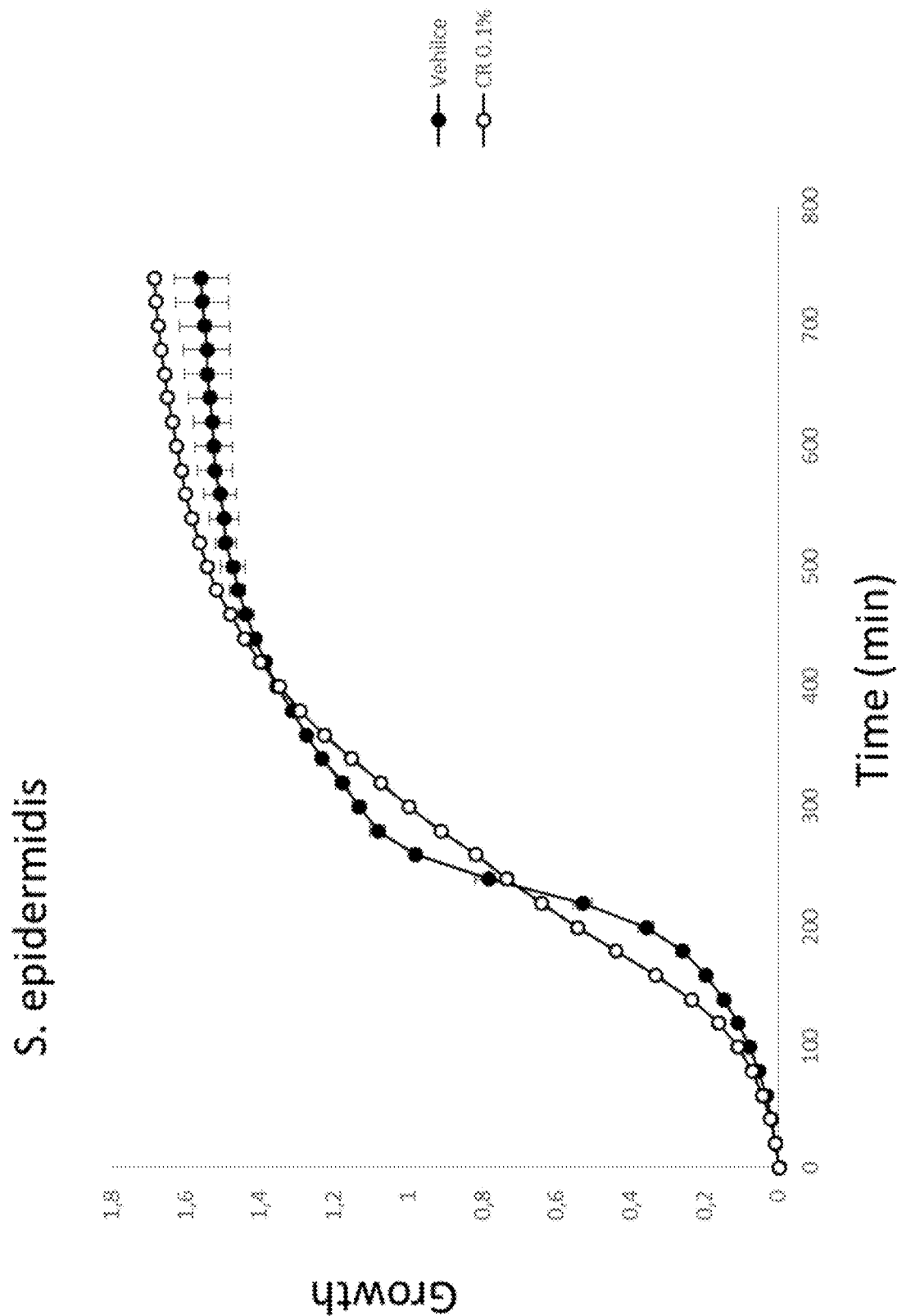
Figure 11E:
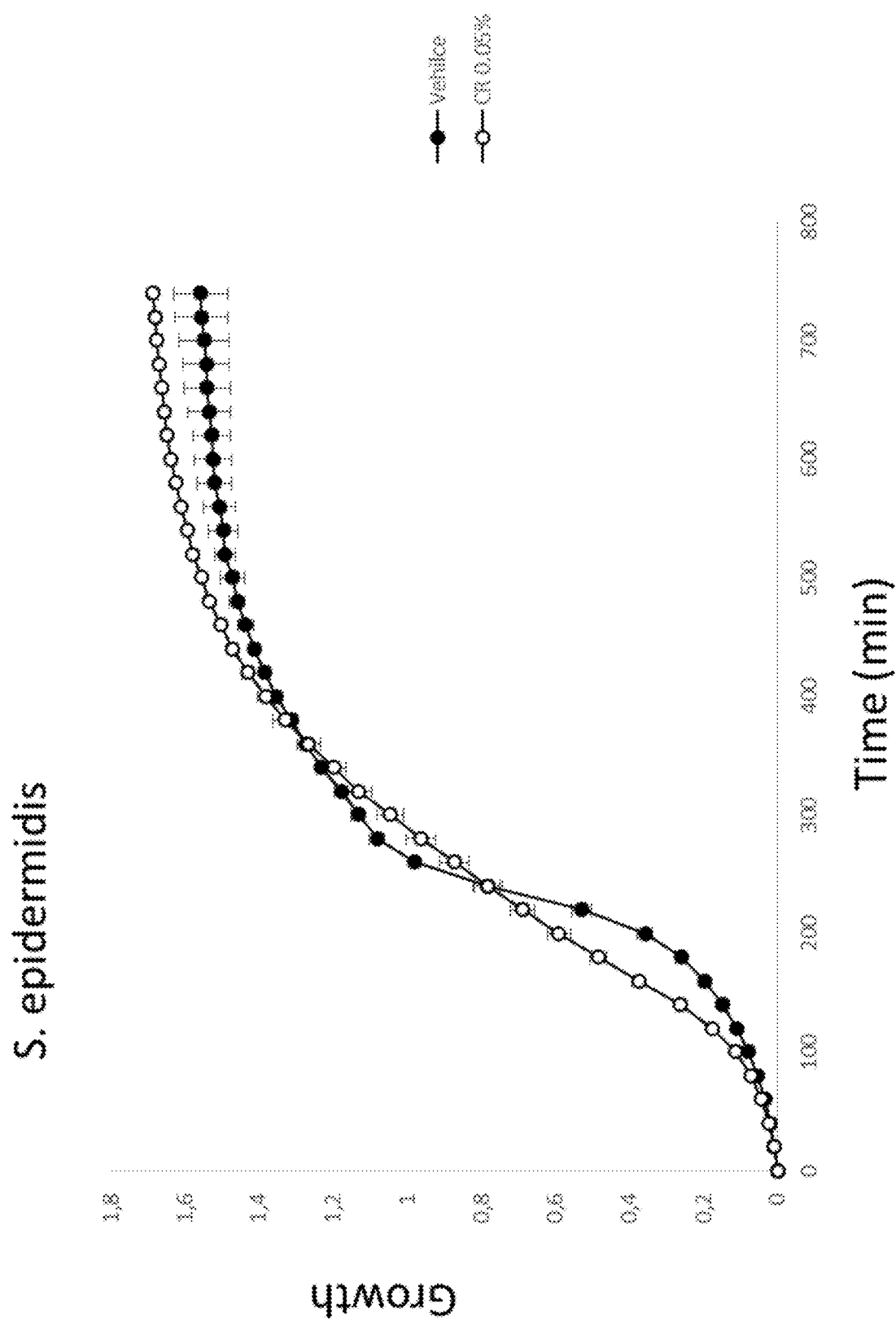
Figure 11F:
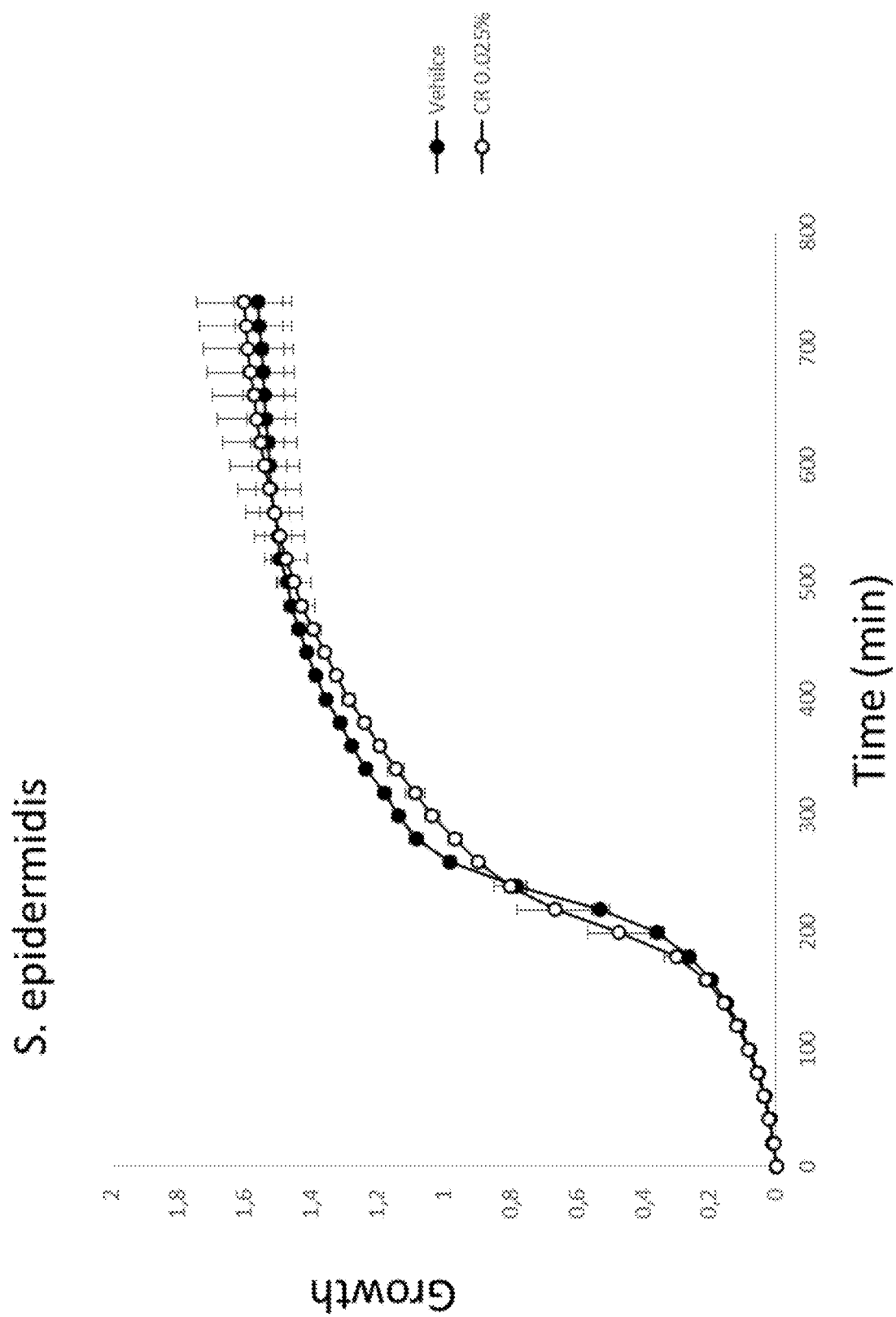
Figure 11G:
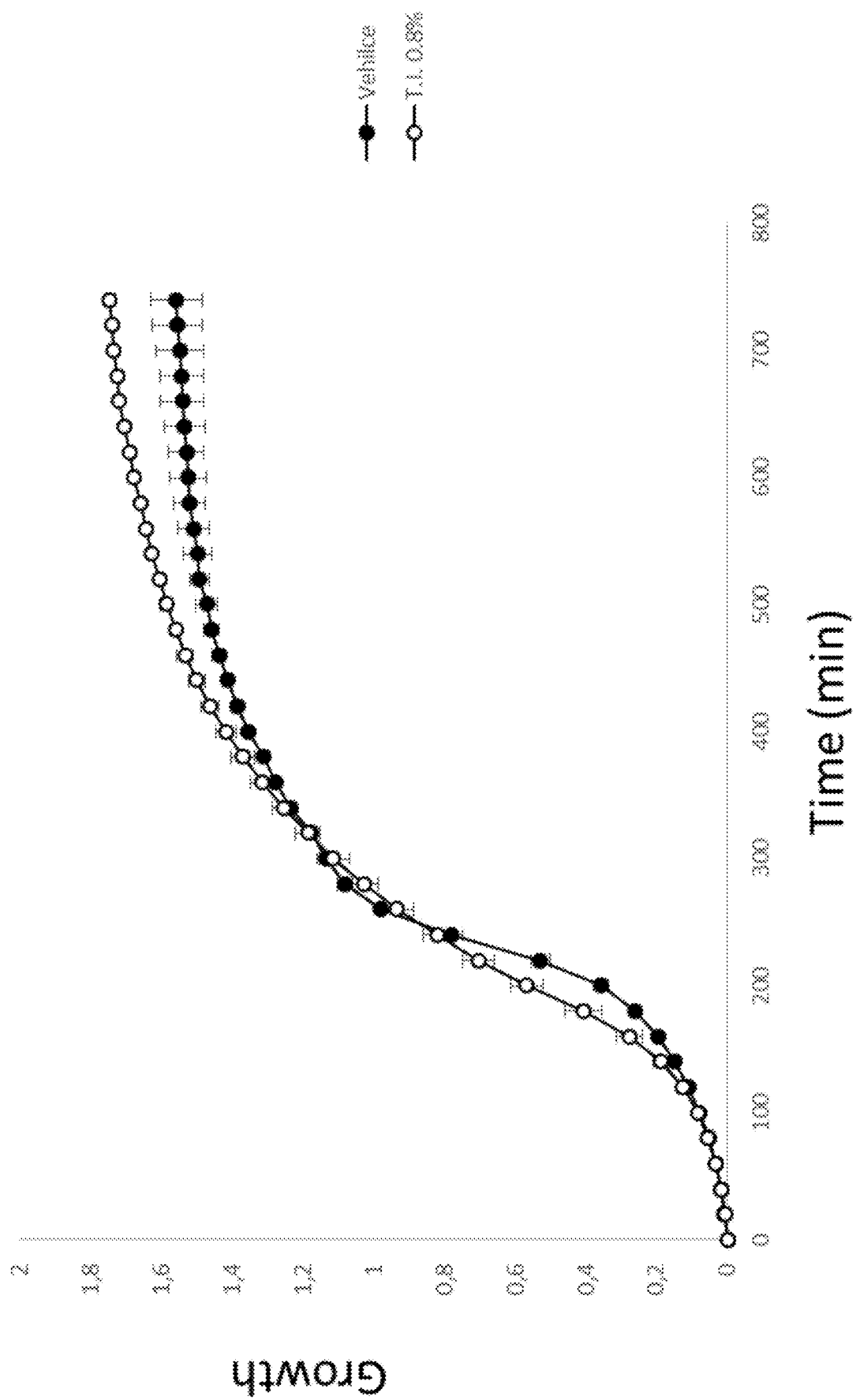
Figure 11H:
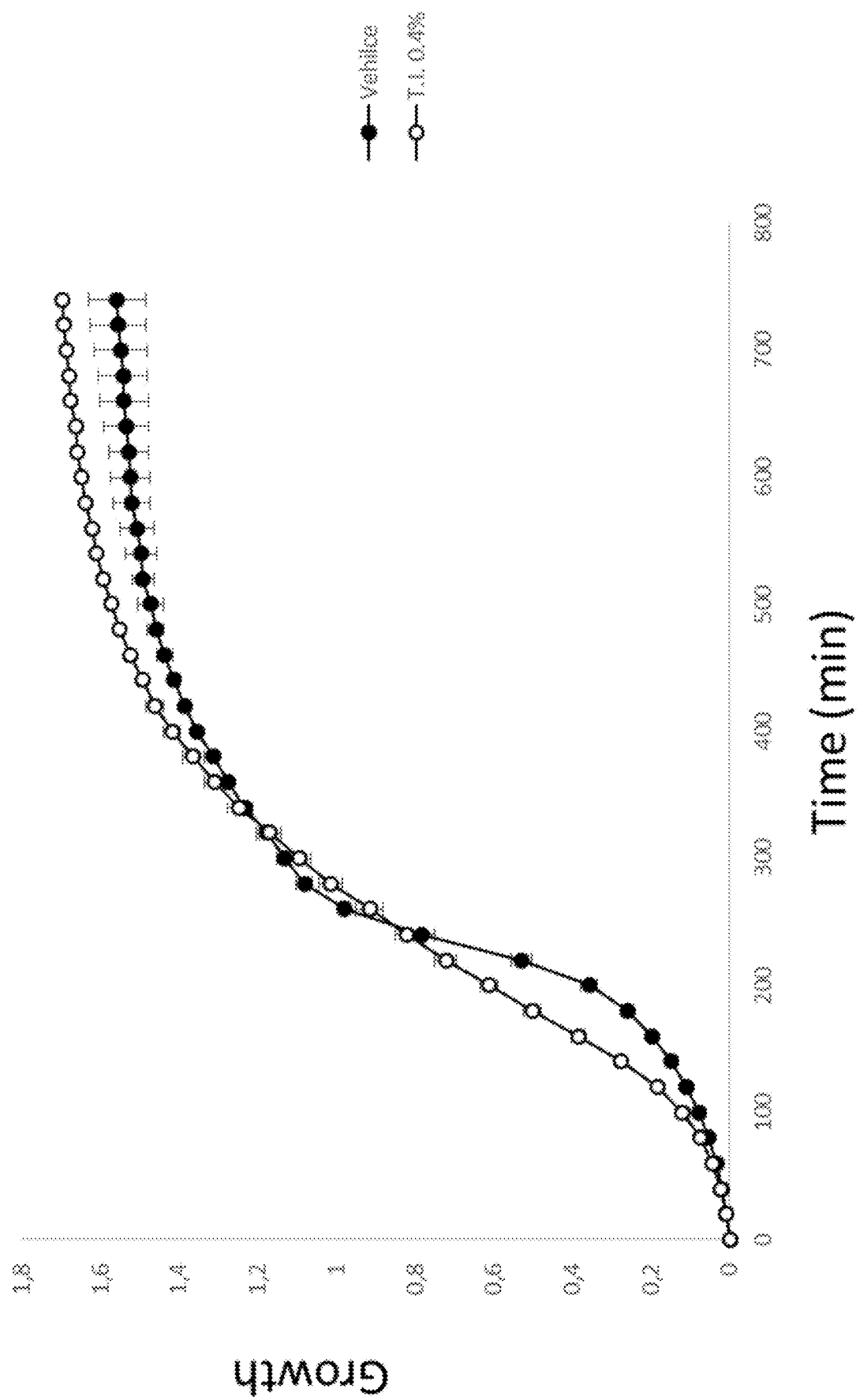
Figure 11I:
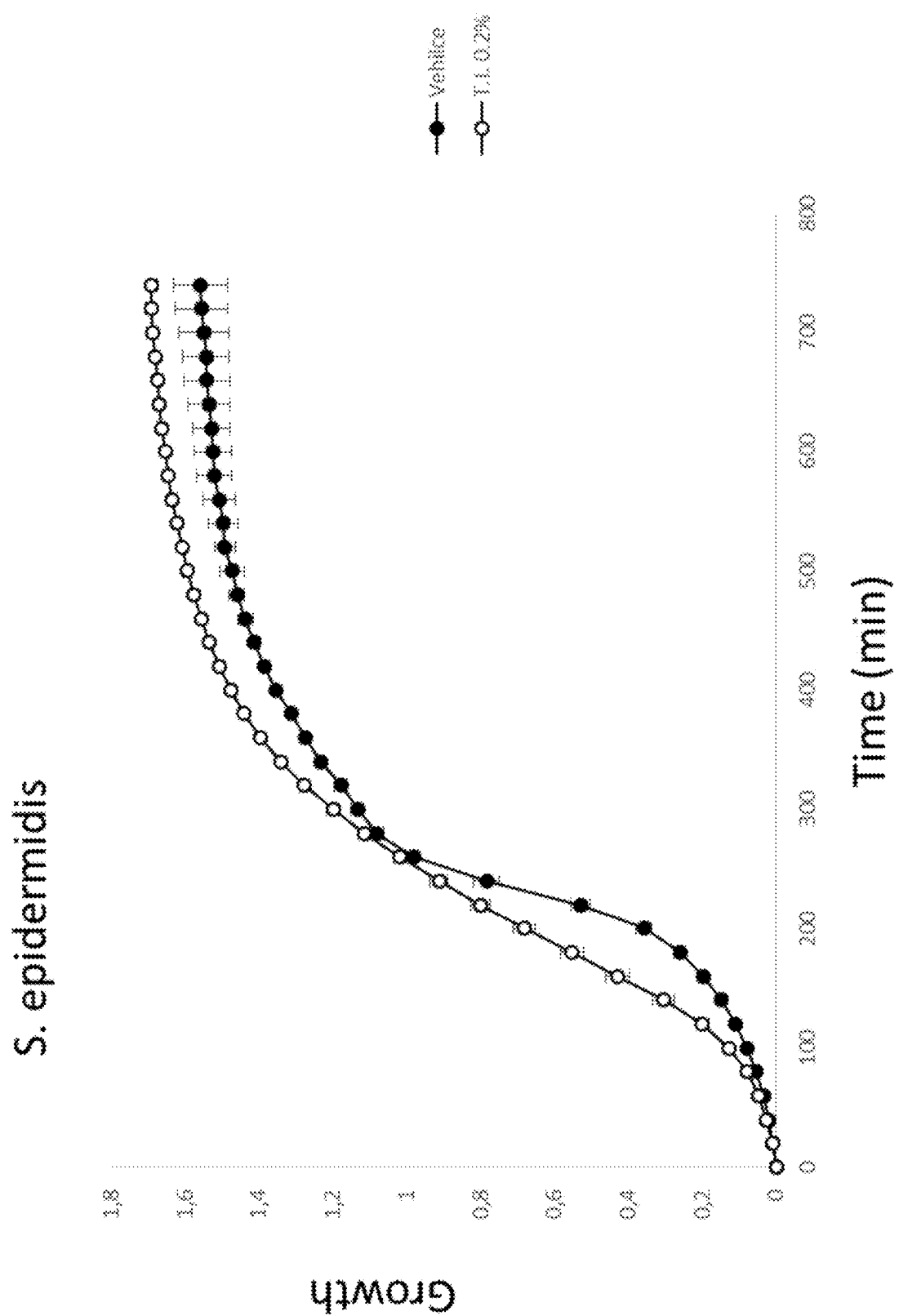
Figure 11J:
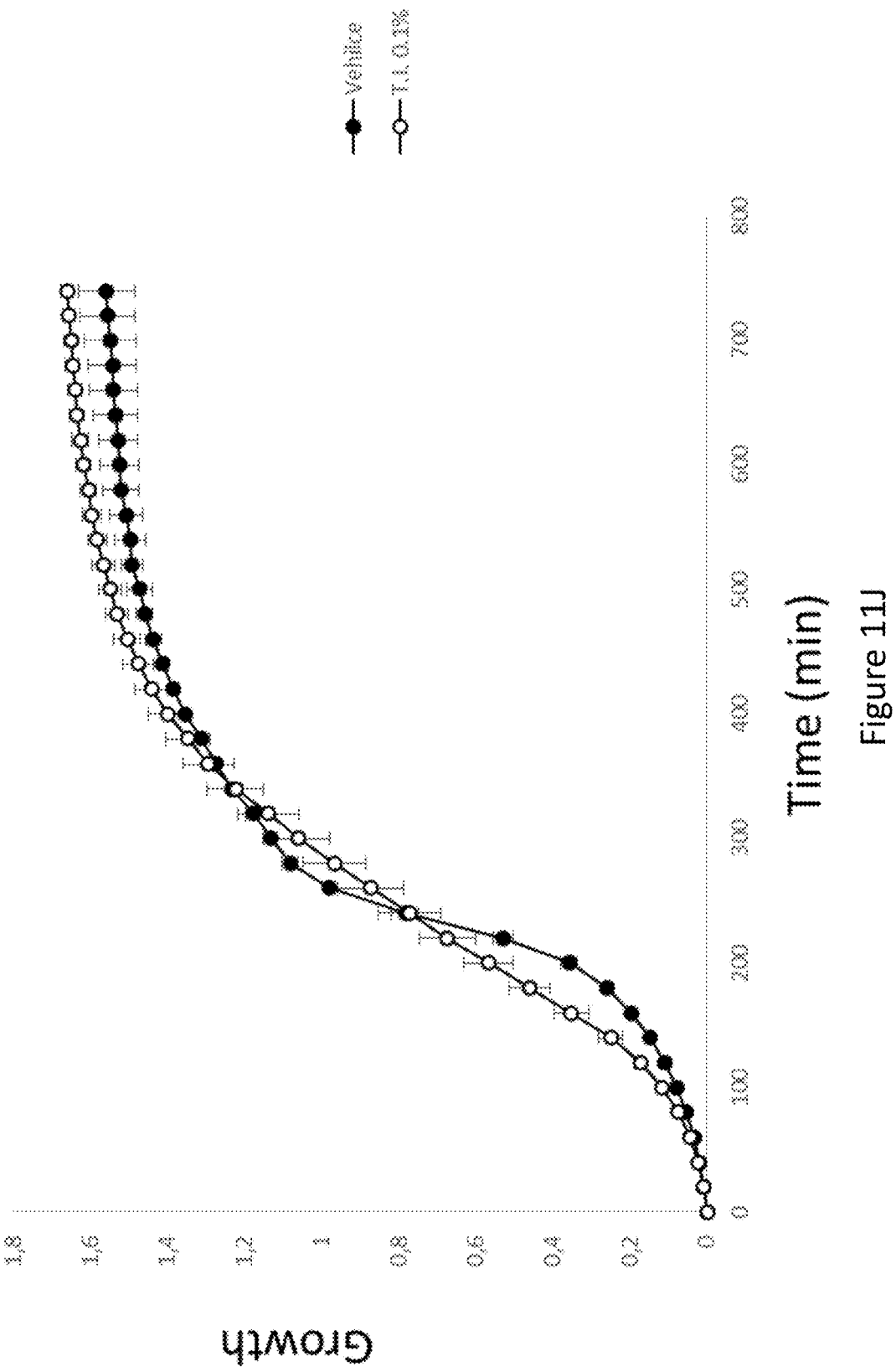
Figure 11K:
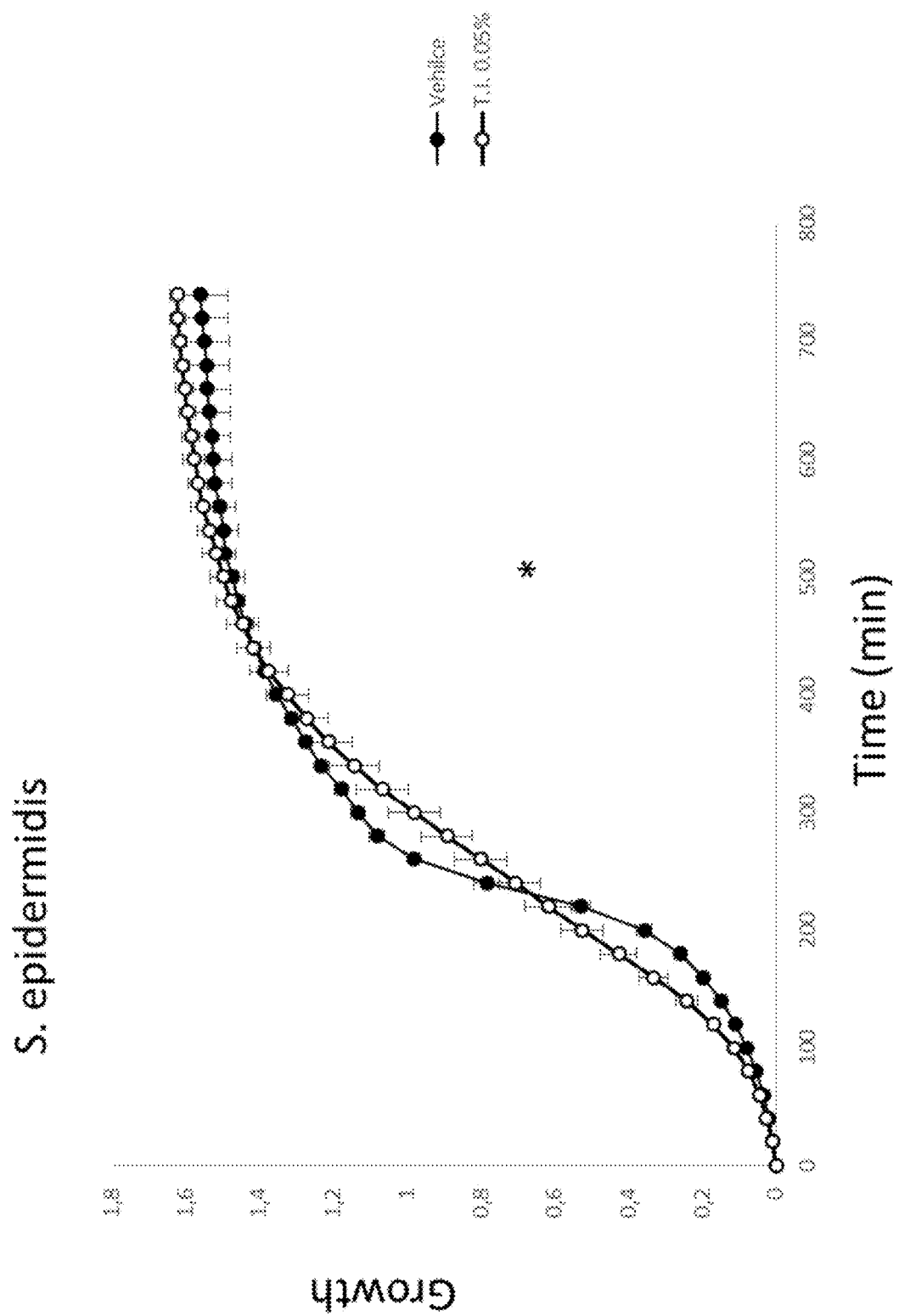
Figure 11L:
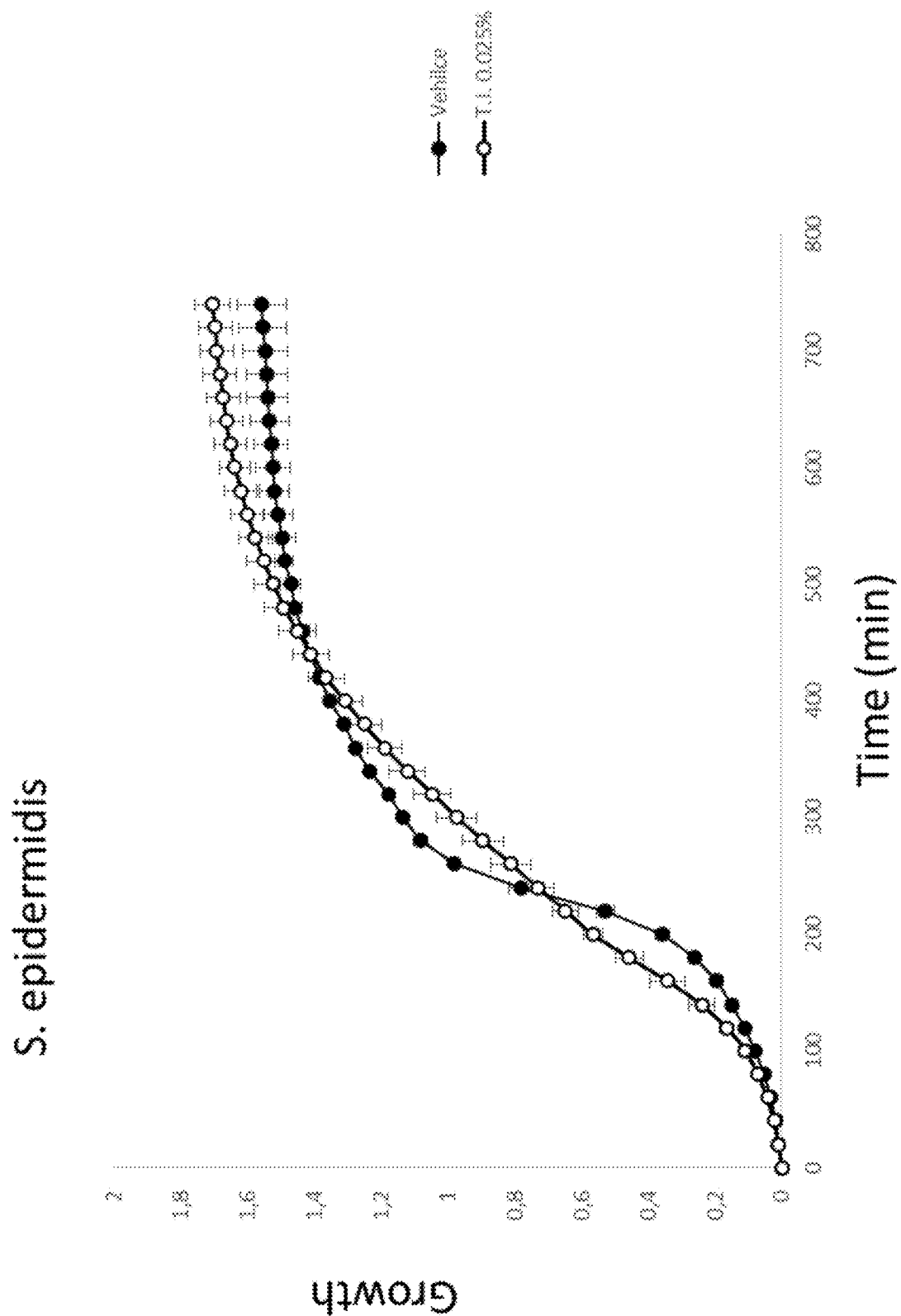
Figure 11M:
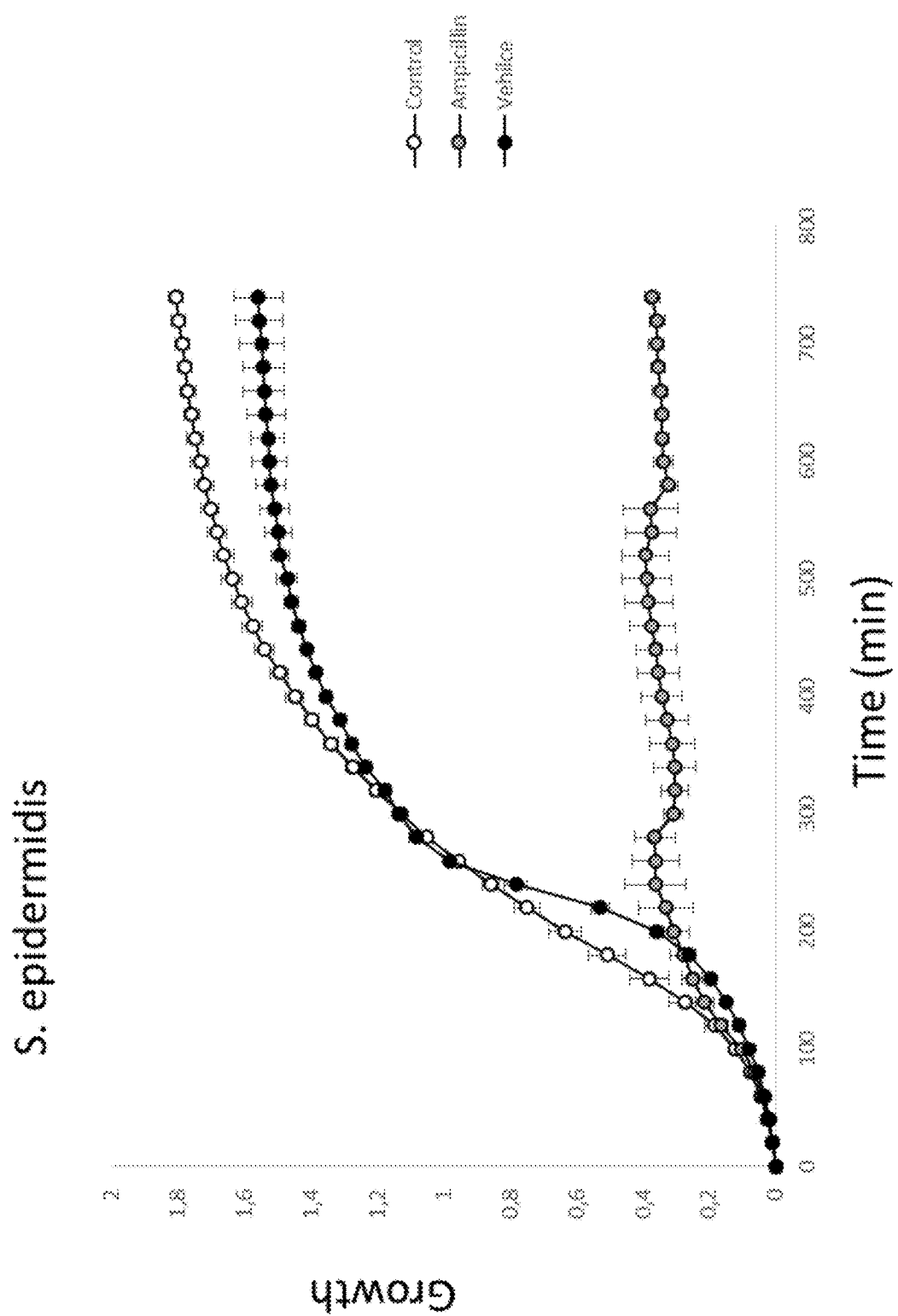

While the C.R exhibited a moderate increase in the proliferation rates, depending on concentration, the Test Item dramatically accelerated the epidermis turnover rates when used at 0.1% and higher. The most prominent effect was observed for the highest concentration (8%), which doubled the proliferation rates (FIG. 10B).

Of note, the Test item effect was significantly higher than the positive control growth factor used in this system (EGF).

Taken together, the Test item and a commercial reference were examined ex vivo on human skin explants.

According to the MTT assay, the safety of the Levan was verified in the ex vivo model. The viability of the skin was not affected by the Test Item at all of the tested concentrations.

In addition, the Test Item was found to accelerate the epidermal proliferation rates. As one of the hallmarks for skin aging is a dramatic slowing down in the keratinocytes turnover, regulating epidermal proliferation is an important feature for a skin rejuvenation-promoting agent.

Although the Commercial Reference (C.R) also showed a positive effect on the epidermal turnover rates, its contribution for acceleration was much moderate in comparison to the Test Item starting from concentration of 0.1%.

To conclude, the disclosed levan-based composition was found to promote skin rejuvenation. In addition, both the HA and commercial reference agents were less effective in this system, thus demonstrating a superior action of the enzymatic-based levan.

Example 3

Prebiotic and Antibacterial Evaluation

The objective of this study was to evaluate the antibacterial effect and possible restoration of the bacterial balance provided by Levan. The bacterial strain used for this screening was *Staphylococcus epidermidis*—gram positive bacteria of normal flora. The Study also included a commercial reference, high molecular weight polysaccharide, to explore possible added value of Levan generated by the enzymatic reaction.

Methods

The material list is presented in Table 6.

TABLE 6

| No./Name | Manufacturer/ Supplier | Cat No./Lot No | Physical State/ storage conditions | Expire date | Name in the report |
|---|---|---|---|---|---|
| Test items | | | | | |
| 1. Baseline solution- | Gan-Shmuel Gan-Shmuel | N/A 4.10.17 | Liquid 2-8° C. | N/A | Vehicle |
| 2. Competitor Levan (commercial reference)- Levan RB | Gan-Shmuel Gan-Shmuel | N/A 4.10.17 | Liquid 2-8° C. | N/A | C.R. |
| 3. Levan | Gan-Shmuel Gan-Shmuel | N/A 4.10.17 | Liquid 2-8° C. | N/A | Test item |
| Chemicals & reagents | | | | | |
| 4. BHI medium | HiMedia Laboratories Hy-Labs | M210-500G 0000220782 | Powder RT | Jan. 2019 | BHI |
| 5. Agar | Hy-Labs Hy-Labs | PW-A/1 5150071 | Powder RT | 30 Apr. 2019 | Agar |
| 6. Ampicillin | Sigma-Aldrich Sigma-Aldrich | A9518 BCBP8492V | Powder 2-8° C. | Jun. 2019 | Ampicillin |
| Bacteria | | | | | |
| 15. Staphylococcus aureus | ATCC Biological industries | 33591 57941605 | Frozen (−70)- (−80)° C. | N/A | S. aureus |
| 16. Staphylococcus epidermidis | ATCC Biological industries | 12228 58532123 | Frozen (−70)- (−80)° C. | N/A | S. epidermidis |

In exemplary procedures, 37 gr powder was dissolved in 1000 ml distilled water. The solution was sterilize by autoclaving.

Ampicillin:

Stock (10 mg/ml): 500 mg of ampicillin was weighed into a 50 ml conical tube. Then, 50 ml of $dH_2O$ was added and vigorously vortex until ampicillin was fully dissolved. Aliquots (1 ml) were kept at −20° C. until use. 100 μg/ml preparation (working solution) was performed at the day of the experiment by dilution 1:100 in the growth broth.

Test Items

The Test items were received sterile and ready to use. The Test items and vehicle control were stored at 2-8° c. until used and diluted in the culture media 1:10 prior of usage.

Test Procedures

Differential Minimal Inhibition Concentration

The aim of this experiment was to evaluate the impact of the Test items on two bacterial strains.

The experiment was conducted in *Staphylococcus epidermidis*. Two Test Items were evaluated in this study; Levan and a Commercial reference (C.R.).

The assay was carried out in triplicates.

The in vitro activity of the Test items was evaluated by minimal inhibition concentration (MIC) assay. This was measured spectrometrically.

The increase bacteria number versus time of incubation w/o or with increasing concentrations of the Test items was plotted.

Streak plate isolation technique was performed to isolate a single homogenous colony, according to SOP.

One colony of each bacterial strain was inoculated from agar plate into U-shape falcon tube at a final volume of 4 ml in BHI liquid broth.

Cultures were incubated in a bacterial incubator-shaker at 37° C. with shaking at 250 rpm overnight. The cultures were diluted and grown to mid-log phase (O.D. Approx. 0.5; 600 nm). The exact O.D. was recorded [0.506]. Dose response analysis of six concentrations for each Test Item was performed in the bacteria as described in Table 7.

The following control groups were included in this study: Naïve group (Group 1), Vehicle group (mock treatment—hexose, Group 2) and positive control groups (Ampicillin (100 μg/ml), Group 3). All test groups and controls were transferred to 96 well plates in triplicates at a final volume of 200 μl. Additional blank control (group 18) was included (media w/o bacteria). The absorbance was recorded at 600 nm.

The absorbance of the blank control was subtracted from all measurements (0.107).

TABLE 7

| Group | Description | Concentration |
|---|---|---|
| 1. | Control naïve | n/a |
| 2. | Vehicle control | n/a |
| 3. | Positive control Ampicillin | 10 μg/ml |
| 4. | Test item | Conc. 1 (0.025%) |
| 5. | | Conc. 2 (0.05%) |
| 6. | | Conc. 3 (0.1%) |
| 7. | | Conc. 4 (0.2%) |
| 8. | | Conc. 5 (0.4%) |
| 9. | | Conc. 6 (0.8%) |
| 10. | | Conc. 1 (0.025%) |
| 11. | | Conc. 2 (0.05%) |
| 12. | | Conc. 3 (0.1%) |
| 13. | C.R. | Conc. 4 (0.2%) |
| 14. | (commercial reference) | Conc. 5 (0.4%) |
| 15. | | Conc. 6 (0.8%) |
| 16. | Blank | n/a |

Results

The Test Item and commercial reference were added in the bacterial culture media at a 1:10 dilution. The vehicle concentration of all groups was set on 10%.

As shown in FIGS. 11A-11M, Ampicillin effectively blocked the bacterial growth of both preparations.

Example 4

Prebiotic Growth Catalyst (Levan)

This study was conducted in order to evaluate if one or more of the tested doses 0.15% Levan of the present invention and 0.30% Levan of the present invention may lead to at least the Average Daily Gain (ADG) and Feed Conversion Ratio (FCR) values of the control group receiving antibiotics according as the standard nutrition protocol on the farm during the end of weaning phase to fatting phase.

The two doses which were tested are: 1.5 kg Levan/1000 kg mixture, that is, 0.15% and 3.0 kg Levan/1000 kg mixture, that is, 0.30%.

The study was carried out in groups of 30-35 piglets per pen (room) between weaning to fattening phase (between the ages of 21-70±5 days). Each pen (room) was used as single repetition in specific study group. The study was carried out as part of the daily antibiotics supplements routine of the farm.

Piglets were selected as the test animals since the Levan is intended to be used as a dietary supplement for pigs.

The antibiotics supplements routine on the farm is *Virginia Miycin* between age 35-70±5 days.

In addition to the normal supplement routine in the farm one Control Group was given *Virginia Miycin* at ages 21-35 days of the piglets.

The Test Items—Levan and *Virginia Miycin* were delivered in the animals' food.

The study consisted of 768 animals, which were divided into 4 experimental groups (about 180 animals in a group, divided into 6 pens (room)):

1. 6 animals' pens that received the prebiotic growth catalyst—Levan in a dose of 0.15% between the animal age 21-70±5 days.
2. 6 animals' pens that received the prebiotic growth catalyst—Levan in a dose of 0.30% between the animal age 21-70±5 days.
3. 6 animals' pens that were a reference group that receives antibiotic growth catalyst—*Virginia Miycin* between the animal age 21-70±5 days.
4. 6 animals' pens that were a control group that receives antibiotic growth catalyst—*Virginia Miycin* between the animal age 35-70±5 days.

The mixture given to the animals was in a form that enabled measurement of the amount of food consumption in each pen—for the purposes of FCR calculation, as detailed below.

The weight of each group was measured at the following times: on the day the experiment begins, on the day of changing the food mixture—age 35 days (±5) of the piglet and on the day the experiment ends.

Observations of morbidity and mortality were carried throughout the study when morbidity is generally assessed by a clinical evaluation of the farm worker and mortality was given as a quantitative number with a limited analysis of the cause of death.

Study termination was on the day ending the weaning phase and the beginning of the fattening phase (age 70 days±5 of the animal or study day 59±5).

Test Item I

Name: Levan

Composition: An aqueous solution containing 28-30% levan, a polyfructose with β-2,6 bonds and a terminal of glucose. About 80% of levan has a molecular weight below 2,000 Daltons. About 20% of levan has a molecular weight above 1Million Daltons.

Characteristics & Physical State:

Levan content: 28-30% w/w

Appearance: Transparent, slightly milky liquid

Odor: Odorless

Solubility: Water soluble

Total sugars (hexoses & sucrose): 30-32%

Acidity (as citric acid): 0.15 0.25%-w/w pH 5.3-5.7

Molecular Weights Distribution 2,000>, 80%~M.W. (by Dionex ion chromatography)

1,000,000<, 20%~M.W. (by SEC-MALLS)

Properties: Humectant, prebiotic

Total Aerobic Microbial Count <$10^3$ cfu/g

Yeast & Mold <$10^2$ cfu/g

Coliforms <10 cfu/g

*E. coli* Absent in 10 g

Reference Item

Name: STAFAC 500

Characteristics & Physical State: solid

Test System

TABLE 8

Animal Information

| | |
|---|---|
| Animals: | Strain- Domestic pigs (*Sus scrofa domestica*) |
| | Sex - females + males |
| | Age - ages of 21 (±5) –70 (±5) days |
| Identification: | Each pen was mark with identification number |

TABLE 9

Constitution of Test Groups

| Group No. | No. of repetitions | Test Items | Dose | Duration | Scheduled |
|---|---|---|---|---|---|
| 1 | n-6 | Levan | 1.5 kg/ton | During all the expenment. | days ±50 |
| 2 | n-6 | Levan | 3 kg/ton | During all the experiment. | |
| 3 | n-6 | Virginia Miycin | | Days 21-35 | |
| | | | 20 gr/ton | Days 35-70 | |
| 4 | n-6 | Virginia Miycin | 20 gr/ton | Days 35-70 | |

Animal Care and Husbandry

Housing: Animal handling is performed according to guidelines of Animal Protection Regulations (Protection of Animals) (Growth pigs and their return for agricultural Purposes). Each pen has maximum 35 animals.

Diet & Water: The animals has free access to food and water. Food was provided through feeders. Drinking water was provided by automatic valves.

Test Item Administration

Route of Administration: The preparation of the Test Items occurs at the beginning of each day. Levan was mixed into the food mixture, according to dosages required by the experimental groups, until a uniform mixture was obtained. Thereafter each pre-mixed mixture was delivered into the animal pens. The food was provided through feeders with free access for the animals.

Dosing Procedure: For Test Group 1 and 2 the food was provided by equivalent sacks (the whole bag will be given to the same pen), mixture by hand with the Test Item in cart. For all Test Groups the food delivered by bucket for each pen and then count the amount of the buckets.

The animals were observed once a day for the duration of the experiment for morbidity, mortality and injury. Morbidity was assessed in general by a clinical evaluation of the farm worker. Mortality was given as a quantitative number. A limited analysis of the cause of death was performed. In addition, veterinarian treatments (vaccinations and medications if necessary) were documented. 6.2 Feed Conversion Ratio—FCR The Feed Conversion Ratio (FCR) was measured by—total weight of eaten food divided by total weight gain of the pen.

Body Weight: The weight of the animals was measured as a pen group of 30-35 animals, during the following times: on the day the experiment began; on the day of the changing of the food mixture—age 35 days±5 of the piglet (day 14 of the study); and on the day the study ended. In case of deceased animals, determination of individual body weights was carried out as close as possible to the time of death, if applicable.

Average Daily Gain—ADG The Average growth rate per animal ADG was measured by—total weight gain of the pen divided by the number of animals divided by the number of days of the experiment.

Evaluation of vitality, leanness and injuries: Evaluation of vitality, leanness ("thinness") and injuries was performed by a farm worker. The evaluation was performed once a week during the entire duration of the study, at pen level. Each study group (groups 1, 2 and 4) was evaluated against the control group at pen-to-pen level (while maintaining consistency in comparison with the different evaluation days). Each pen in the control group received a score of 0 on each assessment day and each pen in the study group was scored against a specific pen of the control group. It is important to note that there is no discernment in the trend of improvement or deterioration between the scoring days, but only in comparison to the control group at each scoring day.

The evaluation was performed according to table 10:

TABLE 10

Group score for vitality, thinness and injuries

| Numerical Grading | |
|---|---|
| -2 | General condition is significantly lower than the control group |
| -1 | General condition is lower to the control group |
| 0 | Control group |
| 1 | General condition is better than the control group |
| 2 | General condition is significantly better than the control group |

For example, on the first day of scoring, each pen in the control group received a score of 0. Randomly, each pen of the study group 1 was compared to a specific pen of the control group, as well as from the study group 2. On the second scoring day, the comparison was performed according to the same pen division performed on the first day of the test.

Humane Endpoints: None of the animals showed sever pain and enduring signs of severe distress.

Termination: Study termination was the last day of the weaning phase and the beginning of the fattening (day 70±5 of the animal) At study termination all animals from the experiment continued to the fattening phase and joined the regular routine.

Results

General Observations

Mortality occurred in all test group and control group:

In group 1—5 piglets were found dead.

In group 2—2 piglets were found dead.

In group 3—2 piglets were found dead.

In group 4—2 piglets were found dead.

This incident had no effect on the study and occurred in all the different groups of the study.

No other abnormal general observations were observed.

Feed Conversion Ratio—FCR, Average Daily Gain—ADG

The analysis of the results for the entire experiment period is shown in table 11.

TABLE 11 summarized analysis of the results

| | 0.15% Levan | 0.30% Levan | Control group 1- Virginia Miycin 20 gr/ton from day 21 | Control group 2- Virginia Miycin 20 gr/ton from day 35 |
|---|---|---|---|---|
| Entrance weight (Kg) | 1074.78 | 1111.7 | 1122.16 | 1159.36 |
| Entrance weight per an individual (Kg) | 5.51 | 5.7 | 6.03 | 6.04 |
| weight at age 35 days (study day - 14) (Kg) | 1664 | 1652 | 1689 | 1770 |
| weight at age 35 days (study day - 14) per an individual (Kg) | 8.58 | 8.56 | 9.08 | 9.22 |
| Finish weight (Kg) | 4873 | 5017 | 4807 | 4917 |
| Finish weight per an individual (Kg) | 25.65 | 25.99 | 26.13 | 25.88 |
| Total weight gain (Kg) | 3798.22 | 3905.3 | 3684.84 | 3757.64 |
| Total weight gain per an individual (Kg) | 20.14 | 20.29 | 20.09 | 19.84 |
| Daily consumption (gr) | 724.55 | 744.09 | 752.51 | 732.29 |
| Average Daily Gain | 440.93 | 446.02 | 439.97 | 434.47 |
| Feed Conversion Ratio (gr/d) | 1.84 | 1.84 | 1.91 | 1.87 |

According to table 11, the Levan (dosage 0.30%) Test group gained:

a. Biggest total weight b. Biggest total weight gain per individual animal.

Control group 1 has the biggest daily consumption and control group 2 has the lowest Average of Daily Gain.

FCR: The best Feed Conversion Ratio appears in both Test Groups 0.15% Levan and 0.30% Levan.

TABLE 12

FCR analysis of the results

| | 0.15% Levan | 0.30% Levan | Control group 1 - Virginia Miycin 20 gr/ton from day 21 | Control group 2- Virginia Miycin 20 gr/ton from day 35 |
|---|---|---|---|---|
| Mean | 1.64 | 1.67 | 1.71 | 1.69 |
| Median | 1.67 | 1.65 | 1.70 | 1.68 |

According to table 12 mean FCR is the highest in Control Group 1, and the lowest in Test Group 0.15% Levan.

Observed body weights were consistent with normal weight gain for domestic pigs under study conditions.

Evaluation of Vitality, Thinness and Injuries

Figure 12A:
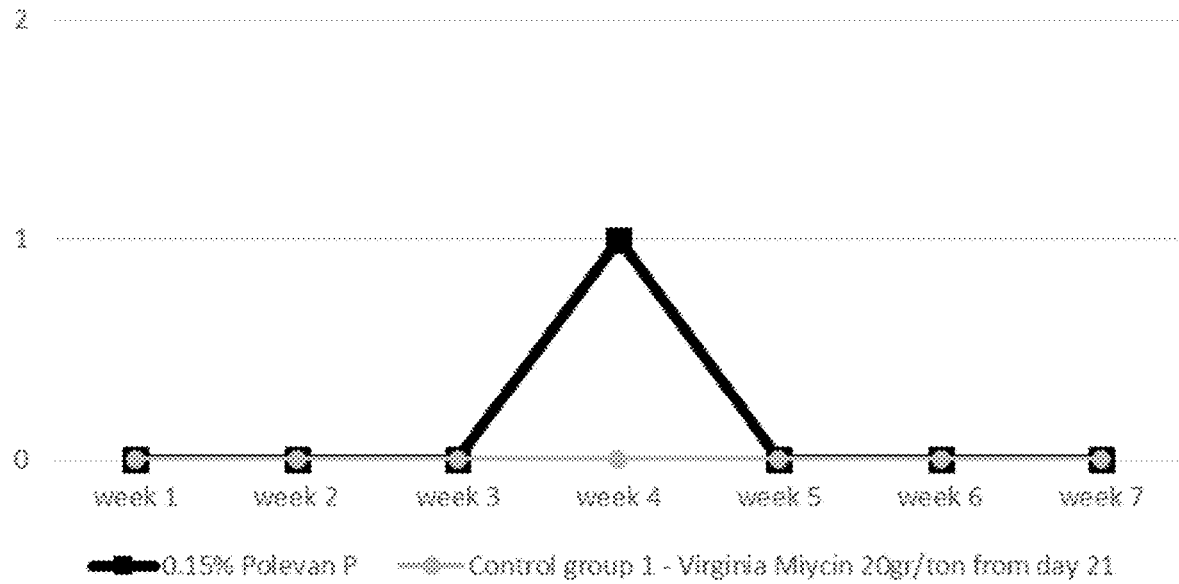
FIGS. 12A-12L present graphs showing the results of vitality, leanness and injuries scores for each test group in rooms (pens) 1-6 from week 1 to week 7 of the study.
Figure 12B:
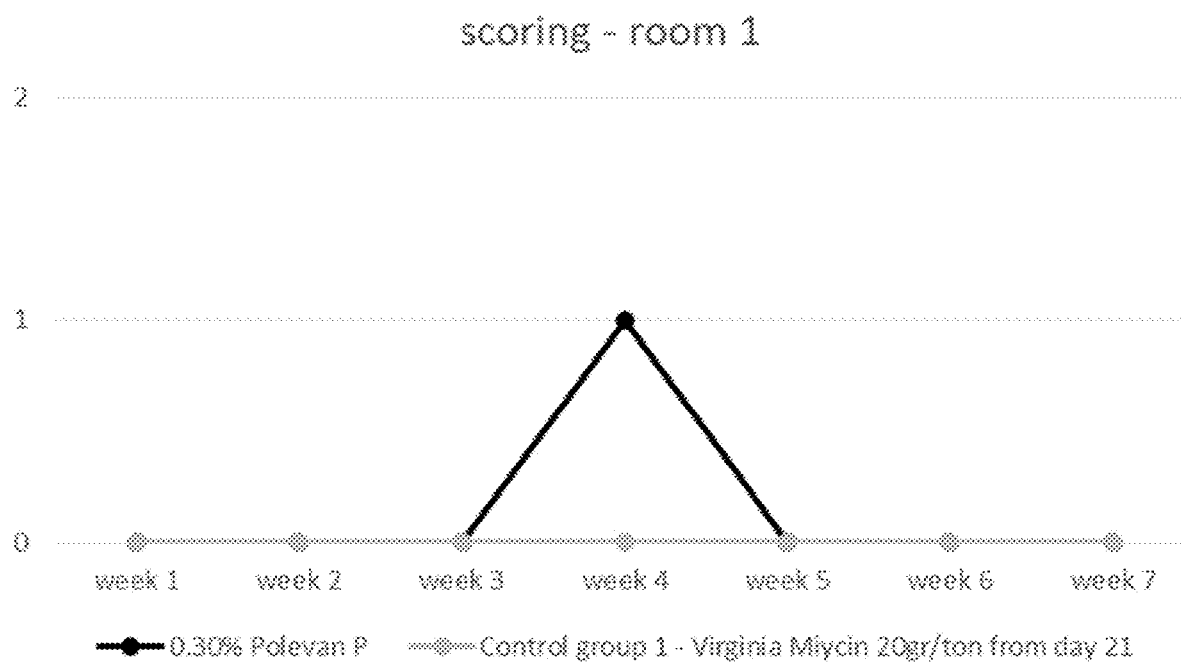

In accordance with FIGS. 12A-12B, 0.15% Levan and 0.30% Levan Test Groups showed one incidence of increasing of vitality, and leanness, and decrease in injuries comparing to control group 1. On the other hand, the control group 2 showed one instance of a decreasing of vitality, leanness and injuries parameters, respectively.

Figure 12C:
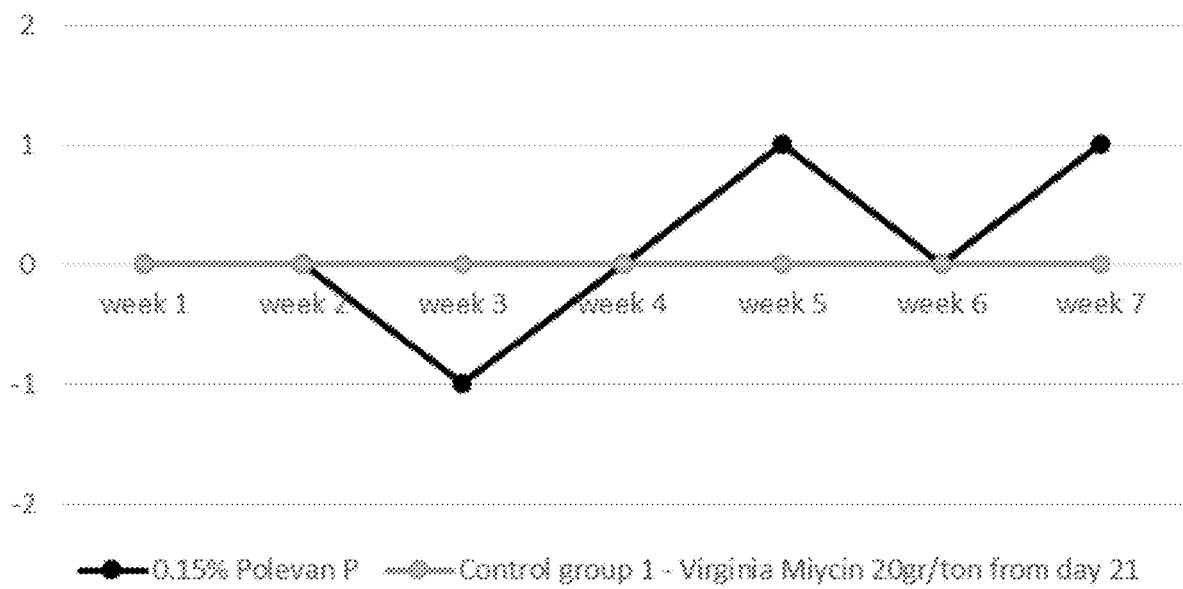
Figure 12D:
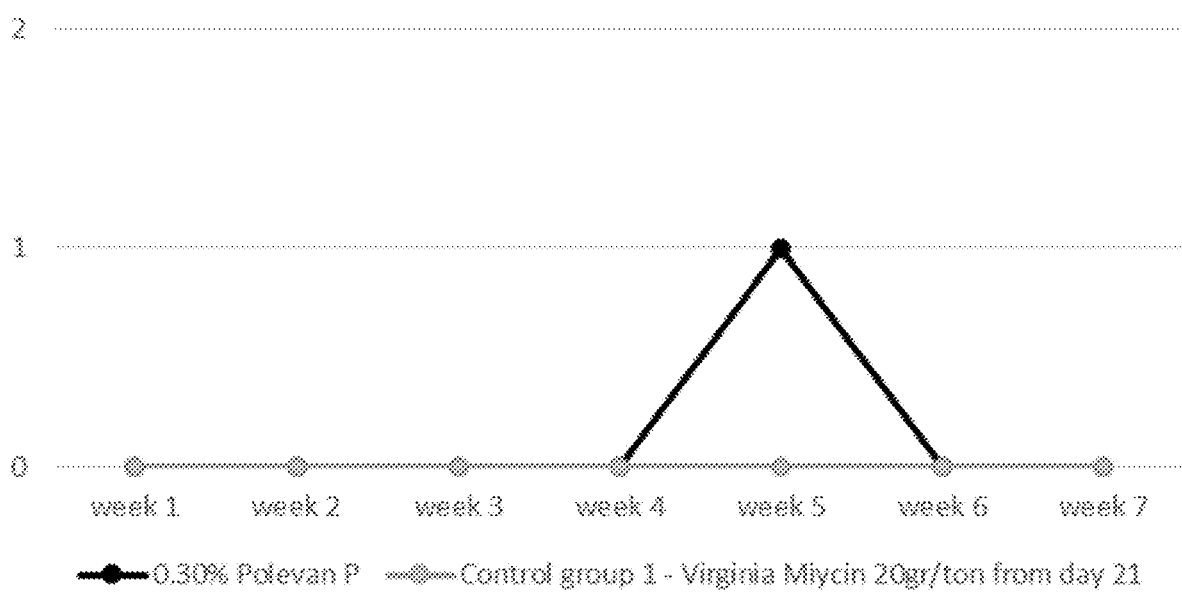

In accordance with FIGS. 12C-12D, 0.30% Levan Test Group showed one incidence of increasing of vitality, leanness and injuries parameters, respectively, compared to control group 1. On the other hand, 0.15% Levan Test Group showed one incidence of decreasing of vitality, leanness and injuries. Control group 2 showed one instance of decreasing and one of increasing of vitality, leanness and injuries.

Figure 12E:
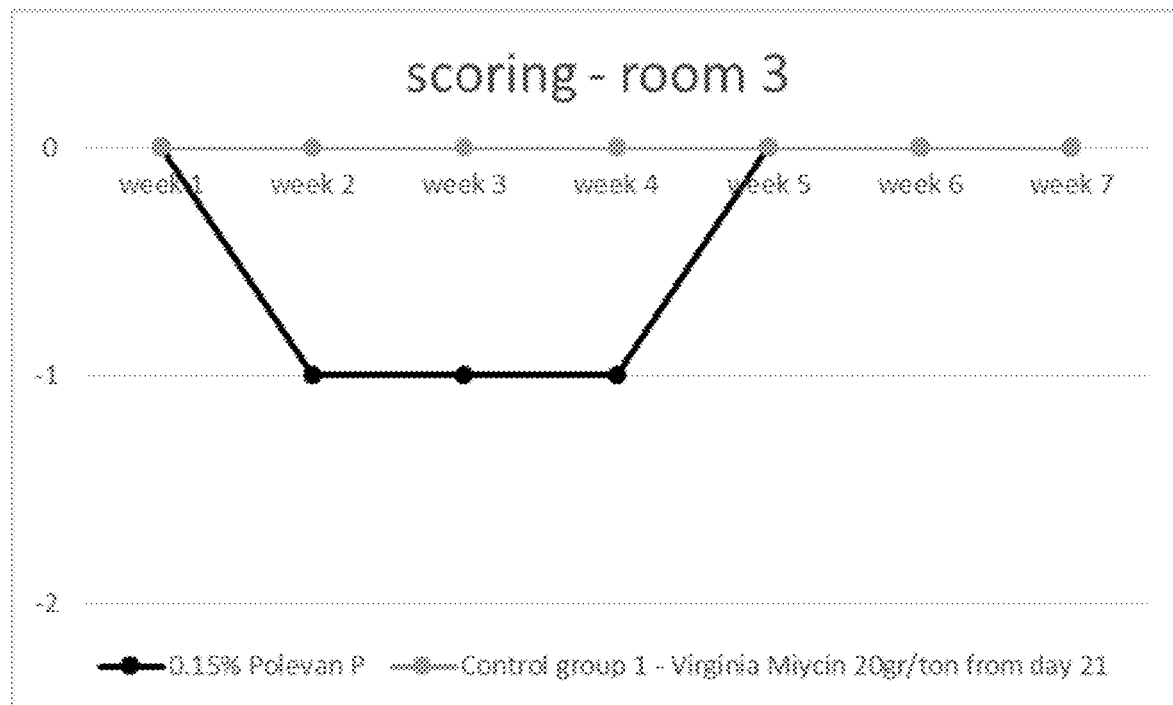
Figure 12F:
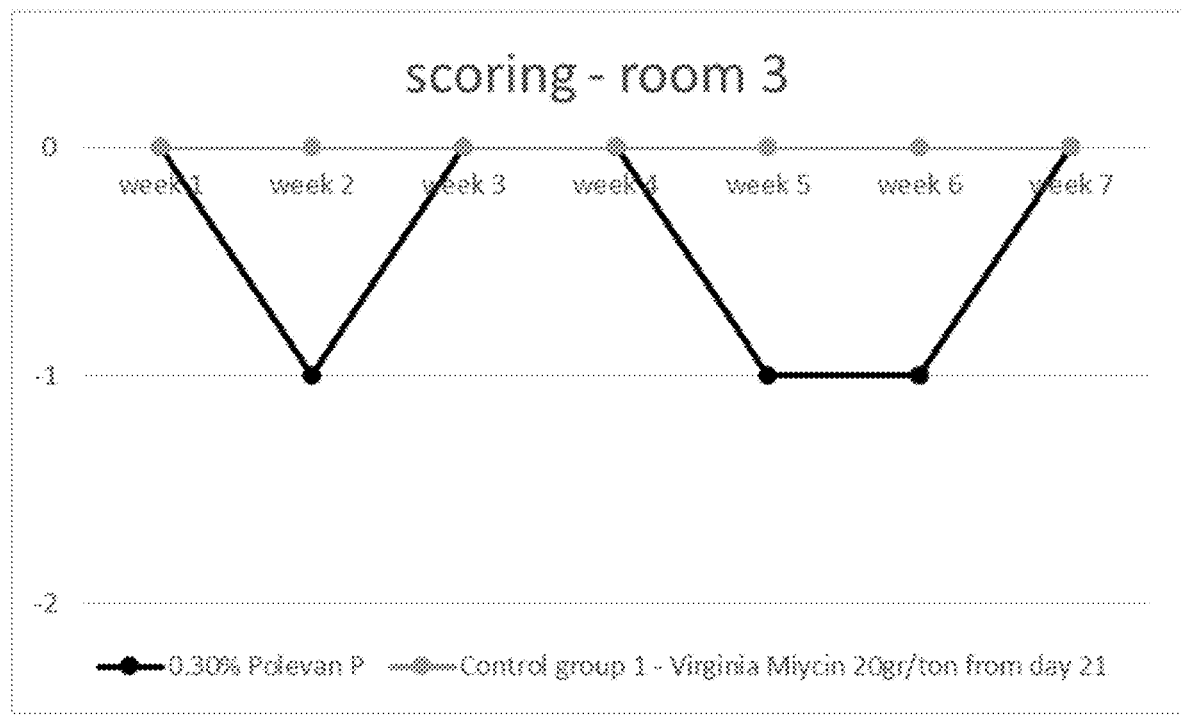

In accordance with FIGS. 12E-12F, 0.15% Levan and 0.30% Levan Test Groups showed three incidences of decreasing of vitality, leanness and injuries compared to control group 1. On the other hand, the control group 2 showed two increasing of vitality, leanness and injuries.

Figure 12G:
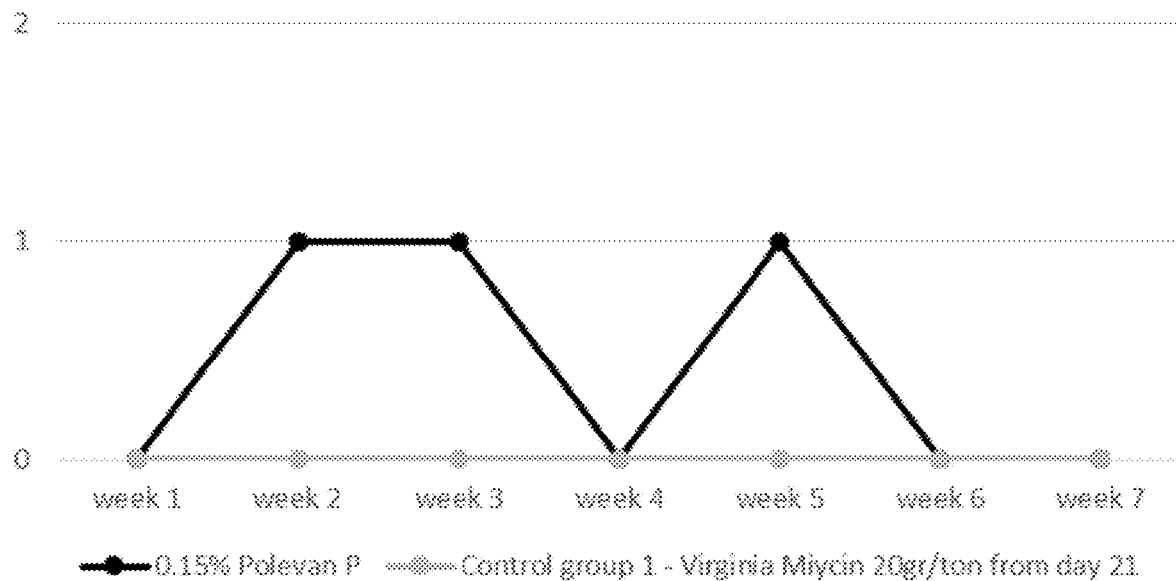
Figure 12H:
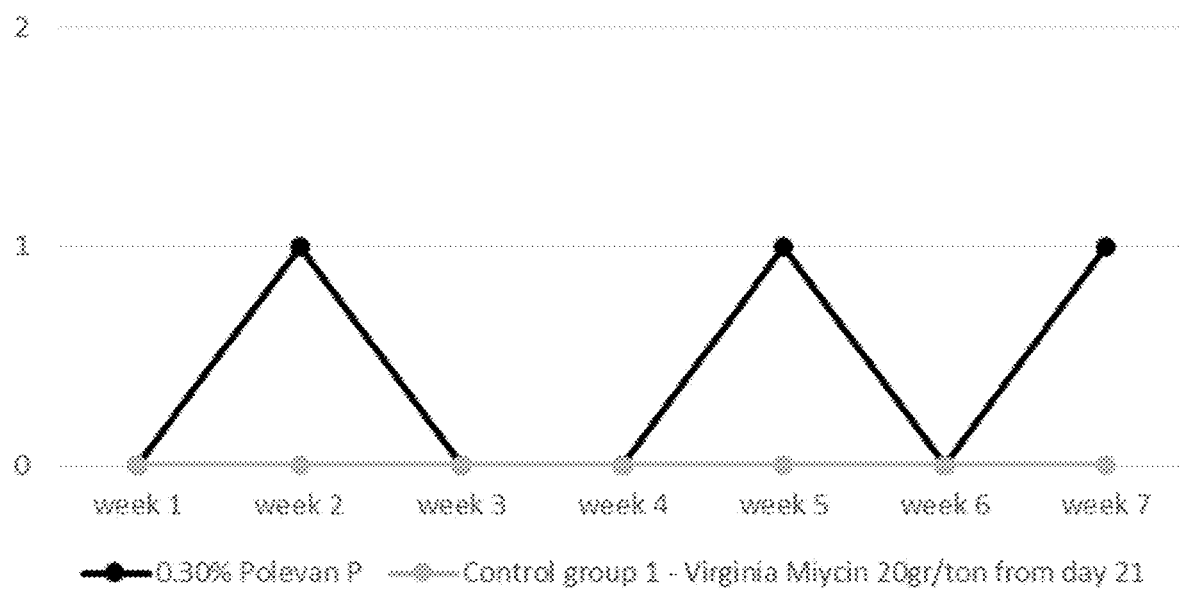
Figure 12I:
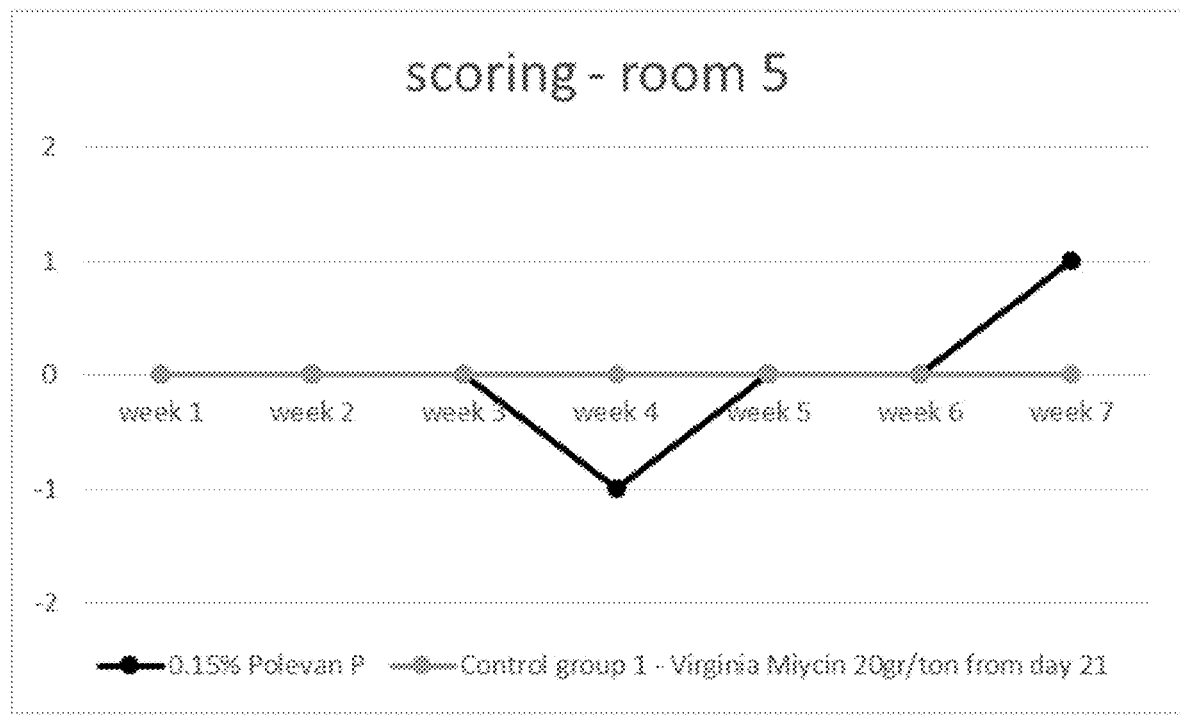
Figure 12J:
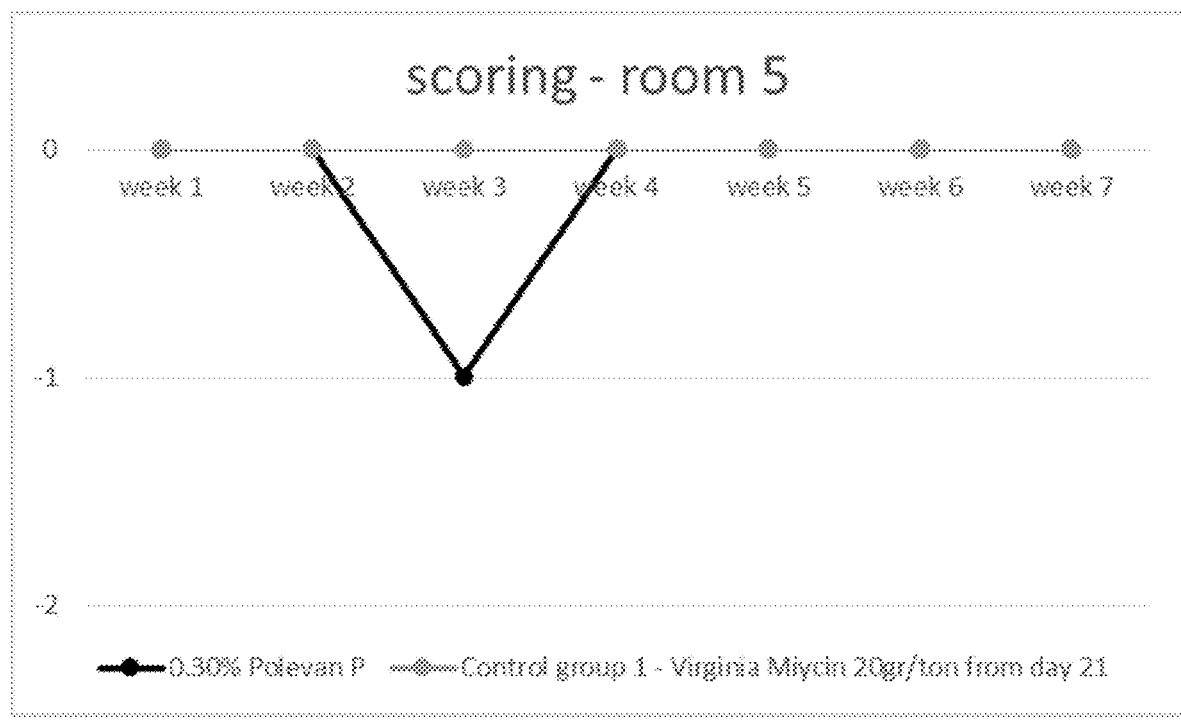

In accordance with FIGS. 12G-12H, 0.15% Levan and 0.30% Levan Test Groups showed two and three respectively, incidences of increasing of vitality leanness and injuries compared to control group 1. Control group 2 showed one instance of decreasing of vitality, thinness and injuries parameters In accordance with FIGS. 12I-12J, 0.30% Levan showed one incidence of decreasing of vitality, leanness and injuries. Control group 2 showed one incidence of increasing of vitality, leanness and injuries compared to control group 1. On the other hand, 0.15% Levan Test Group showed one incidence of decreasing of vitality, leanness and injuries, and one incidence of an increasing of vitality, leanness and injuries.

Figure 12K:
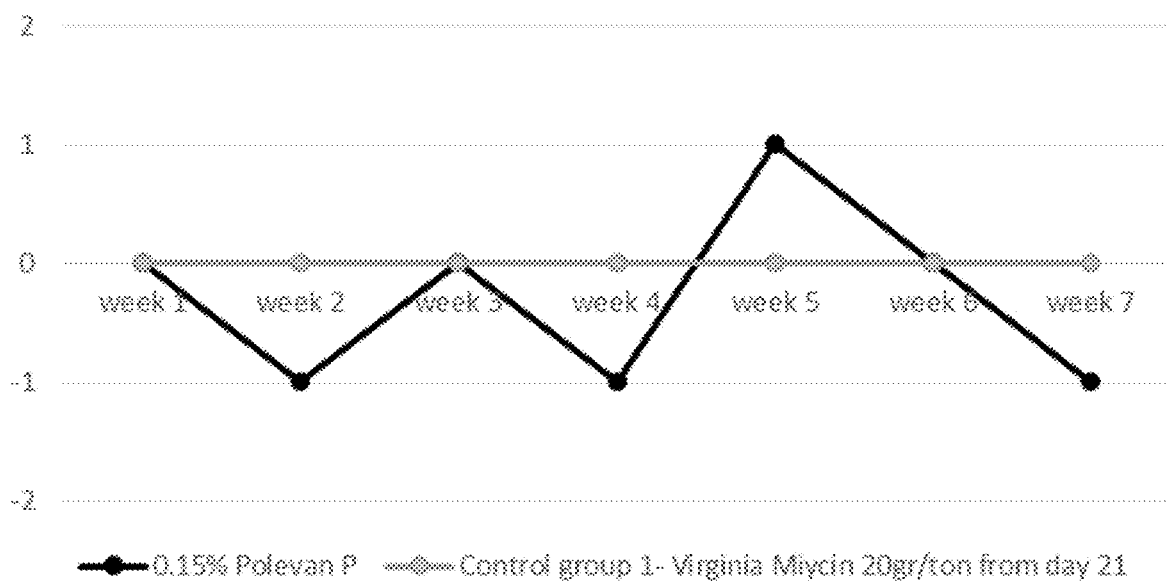
Figure 12L:

In accordance with FIGS. 12K-12L, 0.30% Levan, and Control group 2 showed one and two respectively, incidences of decreasing of vitality leanness and injuries— compared to control group 1. 0.15% Levan Test Group showed one increasing incident and two decreasing incidences of vitality, leanness and injuries.

No abnormal signs were observed, which required the study to be stopped.

Under the conditions of this study it appears through observation that the efficacy of Test Item Levan—as expressed in terms of FCR, ADG and Total Weight Gain— matches that of the antibiotic growth enhancer—the Control Item *Virginia Miycin*.

This statement is not based on statistical analysis but rather on observation only.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A composition comprising levan, wherein said levan is β-2,6 levan consisting of a plurality of levan oligomers and between 1 and 30% levan polymers, by total moles of said oligomers and said polymers, wherein said levan polymers are characterized by MW of above 10,000 g/mol, wherein at least 70% (w/w) of said plurality of levan oligomers are characterized by: (i) weight average molecular weights (MW) of 540 to 1000 g/mol, and (ii) a dispersity index (D) of less than 2.

2. The composition of claim 1, wherein the MW of said polymers is above 30,000 g/mol.

3. The composition of claim 1, wherein said oligomers are characterized by less than 1% branching.

4. The composition of claim 1, wherein said polymers are characterized by less than 10% branching.

5. The composition of claim 1, wherein at least 60% of said levan polymers are in the form of an aggregate having an apparent relative density of 20 to 50.

6. The composition of claim 1, being a cosmetic or cosmeceutical composition.

7. The composition of claim 6, wherein said composition is formulated for topical administration.

8. The composition of claim 7, formulated in the form selected from the group consisting of: aqueous solution, cream, lotion, water in oil or oil in water emulsion, multiple emulsion, silicone emulsion, microemulsion, foam, gel and an aqueous solution with a co-solvent.

9. The composition of claim 1, further comprising one or more components selected from the group consisting of: monosaccharides, disaccharides, buffer, a preservative, one or more additives, or any combination thereof.

10. The composition of claim 1, wherein said levan oligomers are present at a concentration of at least 0.1%, by weight relative to a total weight of the total composition.

11. The composition of claim 1, wherein a total concentration of said levan oligomers and said levan polymers is at least 0.3%, by weight relative to a total weight of the total composition.

12. The composition of claim 11, wherein a total concentration of said levan oligomers and said levan polymers is at least 30%, by weight relative to a total weight of the total composition.

13. The composition of claim 9, wherein a weight ratio of a total amount of said levan oligomers and said levan polymers to said mono- and/or di-saccharides is at least 1.

14. The composition of claim 9, wherein said monosaccharides are selected from the group consisting of: glucose, fructose, and a combination thereof.

15. The composition of claim 9, wherein said one or more additives are present at a concentration of less than 5% by weight relative to a total weight of the composition.

16. The composition of claim 1, for use as a food additive, dietary supplement, feed additive, or prebiotics.

17. A method for improving a skin condition, the method comprising the step of applying the composition of claim 9 to the skin.

18. The method of claim 17, wherein the skin condition is selected from the group consisting of: improving the rejuvenation and healing of skin, fine lines, wrinkles, discoloration, uneven pigmentation, sagging, enlarged pores, blemishes, and a combination thereof.

19. A method for improving feed conversion ratio, the method comprising the step of providing feed comprising the composition of claim 9 to an animal.

\* \* \* \* \*